US007818041B2

(12) United States Patent
Kim et al.

(10) Patent No.: US 7,818,041 B2
(45) Date of Patent: Oct. 19, 2010

(54) SYSTEM AND METHOD FOR EFFICIENT DIAGNOSTIC ANALYSIS OF OPHTHALMIC EXAMINATIONS

(76) Inventors: Young Kim, 13103 Frog Hollow Ct., Herndon, VA (US) 20171; Ken Lee, 2603 Hannah Farm Ct., Oakton, VA (US) 22124; Imran Noor Chaudhri, 10801 Brickyard Ct., Potomac, MD (US) 20854

( * ) Notice: Subject to any disclaimer, the term of this patent is extended or adjusted under 35 U.S.C. 154(b) by 914 days.

(21) Appl. No.: 11/175,410

(22) Filed: Jul. 7, 2005

(65) Prior Publication Data
US 2006/0025670 A1 Feb. 2, 2006

Related U.S. Application Data

(60) Provisional application No. 60/585,568, filed on Jul. 7, 2004.

(51) Int. Cl.
*A61B 5/05* (2006.01)
(52) U.S. Cl. .................. 600/407; 600/437; 600/410; 600/425; 600/440; 600/463
(58) Field of Classification Search .................. None
See application file for complete search history.

(56) References Cited

U.S. PATENT DOCUMENTS

| 5,179,651 | A | * | 1/1993 | Taaffe et al. ............... 345/555 |
| 5,327,341 | A |   | 7/1994 | Whalen et al. |
| 5,581,460 | A |   | 12/1996 | Kotake et al. |
| 5,732,221 | A |   | 3/1998 | Feldon et al. |
| 6,032,120 | A | * | 2/2000 | Rock et al. .................... 705/2 |
| 6,260,021 | B1 | * | 7/2001 | Wong et al. .................... 705/2 |
| 6,381,557 | B1 | * | 4/2002 | Babula et al. ............... 702/183 |
| 6,524,245 | B1 | * | 2/2003 | Rock et al. .................. 600/437 |
| 6,581,069 | B1 | * | 6/2003 | Robinson et al. ......... 707/104.1 |
| 2002/0188896 | A1 |   | 12/2002 | Filteau et al. |
| 2003/0016850 | A1 |   | 1/2003 | Kaufman et al. |
| 2005/0010859 | A1 |   | 1/2005 | McDonough et al. |
| 2005/0021413 | A1 |   | 1/2005 | Berry et al. |

(Continued)

OTHER PUBLICATIONS

Daniel Ertman,(Oxalis: a distributed, extensible ophthalmic image annotations system), thesis presented to school of engineering, University of Pittsburg, Mar. 26, 2003.*

(Continued)

*Primary Examiner*—Long V Le
*Assistant Examiner*—Joel F Brutus
(74) *Attorney, Agent, or Firm*—Edell, Shapiro & Finnan, LLC

(57) ABSTRACT

A digital medical diagnostic system according to the present invention enables ophthalmologists to view patient and other images remotely to diagnose various conditions. The system includes at least one modality, one or more viewing stations, and an image server. The modality generates patient images associated with examinations, while the image server retrieves and processes information from the modalities. The image server may accommodate modalities utilizing different interfaces and/or formats. The viewing stations enable remote access to the images via a network (e.g., Internet), where the image server provides the interface for a user in the form of screens or web pages for security and viewing of information. The system enables an ophthalmologist or other medical personnel to view and/or manipulate one or more images to enhance diagnosis of patient examinations.

56 Claims, 24 Drawing Sheets

U.S. PATENT DOCUMENTS

| | | |
|---|---|---|
| 2005/0096530 A1 | 5/2005 | Daw et al. |
| 2005/0107689 A1 | 5/2005 | Sasano |
| 2005/0107690 A1 | 5/2005 | Soejima |
| 2005/0120300 A1 | 6/2005 | Schwager et al. |
| 2005/0197860 A1 | 9/2005 | Joffe et al. |
| 2005/0265588 A1 | 12/2005 | Gholap et al. |
| 2006/0064321 A1 | 3/2006 | Sasano et al. |
| 2006/0136269 A1 | 6/2006 | Fraser |
| 2006/0242143 A1 | 10/2006 | Esham et al. |
| 2006/0242149 A1 | 10/2006 | Richard |
| 2008/0071576 A1 | 3/2008 | Berry et al. |
| 2009/0048833 A1 | 2/2009 | Fritsch et al. |

OTHER PUBLICATIONS

Long et al (Design considerations for wide area distribution of digital X-ray images), PACS design and evaluation Proc. SPIE vol. 1899, Medical Imaging, 1993, pp. 383-394.*

Yannuzzi et al., Ophthalmic Fundus Imaging: Today and Beyond, Google 2004, pp. 511-524.

Lim et al., A Web-based Collaborative System for Medical Image Analysis and Diagnosis, ACM 2001, pp. 93-95.

Kim et al., "A Solution to the Distribution and Standardization of Multimedia Medical Data in E-Health", ACM 2002, pp. 1-4.

* cited by examiner

FIG. 7

SYSTEM AND METHOD FOR EFFICIENT DIAGNOSTIC ANALYSIS OF OPHTHALMIC EXAMINATIONS

CROSS-REFERENCE TO RELATED APPLICATIONS

This application claims priority from U.S. Provisional Patent Application Ser. No. 60/585,568, entitled "System and Method for Efficient Diagnostic Analysis of Ophthalmic Examinations" and filed Jul. 7, 2004, the disclosure of which is incorporated herein by reference in its entirety.

BACKGROUND OF THE INVENTION

1. Technical Field

The present invention relates generally to the field of medical diagnostic systems. In particular, the present invention relates to a digital medical diagnostic system designed to allow ophthalmologists to efficiently diagnose patients based on ophthalmic examinations.

2. Discussion of Related Art

Many digital medical diagnostic and imaging systems exist in modern ophthalmology facilities. Such systems provide invaluable tools for identifying, diagnosing and treating ophthalmic diseases. Often, final diagnosis and treatment proceed only after the ophthalmologist has reviewed examinations with detailed images of relevant patient areas and tissues via one or more imaging modalities.

Currently, there are quite a few digital modalities that can be used for ophthalmic diagnosis. These modalities include, but are not limited to, the following: Fundus Cameras for angiography, color photos and red free photos; Ultrasound; Optical Coherence Tomography; Slit-lamp photography; Corneal Topography; and Scanning Laser Ophthalmosocope. These modalities complement one another and offer the ophthalmologist a range of techniques for imaging particular diseases. Further, these modalities are stand-alone systems, or have just a limited ability to provide local networking functions.

The conventional ophthalmology modality environment is illustrated in FIG. 1. The typical ophthalmic facility contains a modality 10 optionally connected to a viewing station 20, via a private network 30. The modality includes image acquisition hardware 11 that is connected to an image-processing capture station or computer system 12. This computer system includes a monitor 13 to directly display the acquired images and a storage subsystem 14 to store a limited number of studies. A study generally refers to a group of images taken at the same time on the same patient. Typically, computer system 12 further includes a mechanism or archive 15 for archiving studies. Studies are archived to free up the limited storage space, to file studies with the physical patient record, and to provide a backup mechanism for retrieving studies in case of a disaster. Current archiving mediums include paper printout, CD, DVD, and tape. Most of the advanced modalities further include a network connection 16. The network connection is used to display studies on a viewing station 20 via private network 30.

Viewing station 20 includes a computer system 22 with a monitor 21 to display the studies, proprietary viewing software 23 and a network connection 24 to communicate with modality 10 via private network 30. Current ophthalmic modalities providing access to studies from viewing stations 20 are based on a client-server architecture that requires modality specific proprietary viewing software 23 on the viewing station. This proprietary software works on private local area network 30, but is inoperable for public or wide area networks which characteristically have low bandwidth and slow response times (large delays). The proprietary software also does not support access to studies by many viewers at the same time.

Ophthalmologists using these modalities need to be near the modalities' physical location and need to use the modalities' proprietary software to perform a diagnosis of the captured examinations. The current scenario has several drawbacks: (1) the ophthalmologist needs to be physically close to the modality; (2) the ophthalmologist needs to install the proprietary software at each location examinations are accessed; (3) the ophthalmologist needs to learn each modality's proprietary software; (4) the ophthalmologist cannot easily compare data from different modalities; and (5) the ophthalmologist must deal with proprietary user interfaces that do not optimize the way ophthalmologists view and diagnose examinations.

SUMMARY OF THE INVENTION

According to the present invention, a digital medical diagnostic system enables ophthalmologists to view patient and other images remotely to diagnose various conditions. The system includes at least one modality, one or more viewing stations, and an image server. The modality generates patient images associated with examinations, while the image server retrieves and processes information from the modalities. The image server may accommodate modalities utilizing different interfaces and/or formats. The viewing stations enable remote access to the images via a network (e.g., Internet), where the image server provides the interface for a user in the form of screens or web pages for security and viewing of information. The system enables an ophthalmologist or other medical personnel to view and/or manipulate one or more images to enhance diagnosis of patient examinations.

The present invention provides several advantages. For example, the present invention: (1) allows ophthalmologists to view images where a public network is available; (2) allows ophthalmologists to use standard https browser software to access examinations; (3) provides a uniform interface for all modalities; (4) allows ophthalmologists to easily compare data from different modalities; and (5) provides a user interface that simplifies and optimizes the way ophthalmologists view and diagnose examinations.

The above and still further features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

Figure 7:
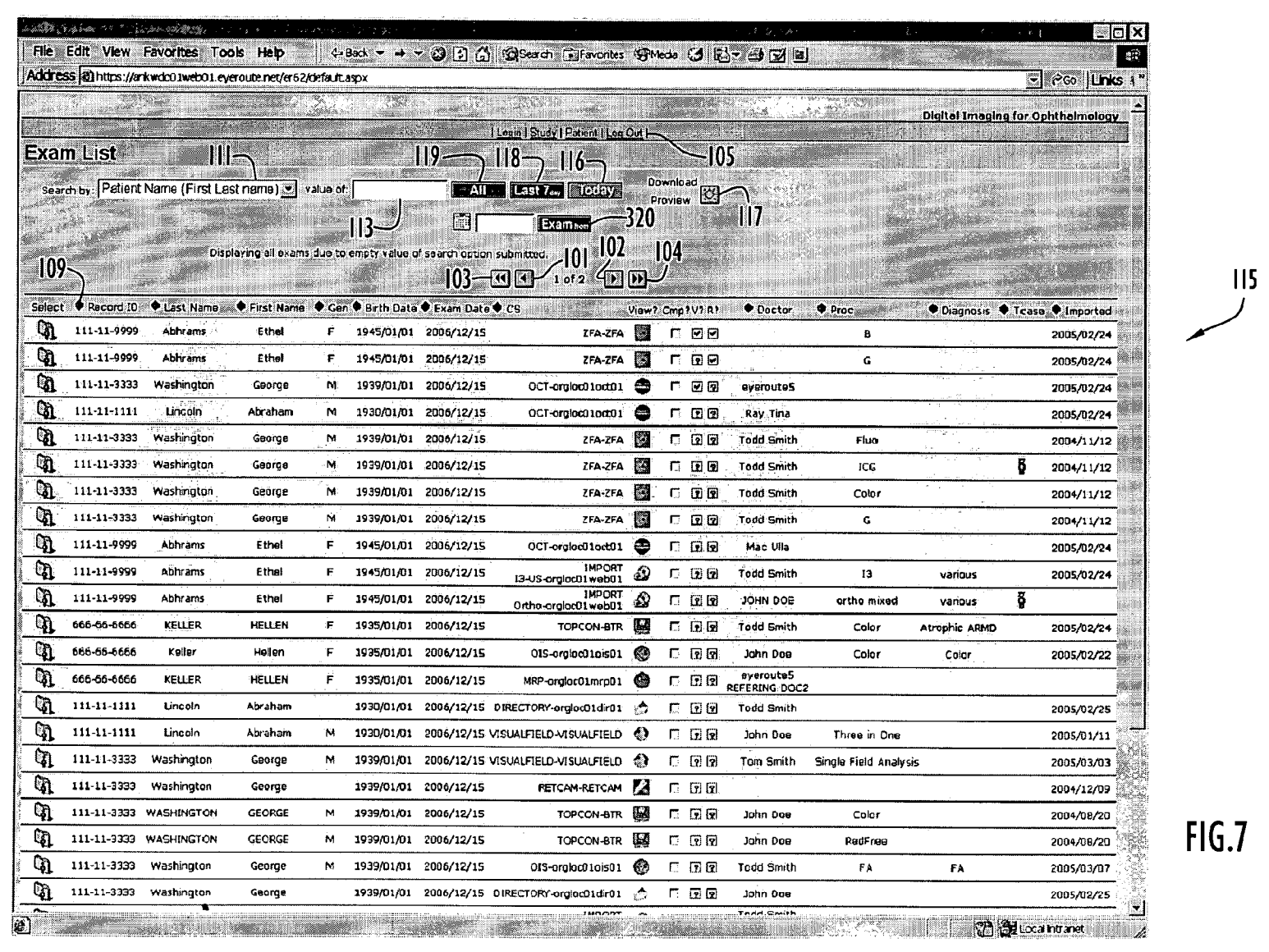

FIG. 7 is an illustration of an exemplary graphical user screen employed by the present invention to display a customized patient list that can be configured according to user preferences.

FIG. 21 is a system flow diagram of the image server integrated with an electronic medical record system according to the present invention.

DETAILED DESCRIPTION OF THE PREFERRED EMBODIMENTS

Figure 1:
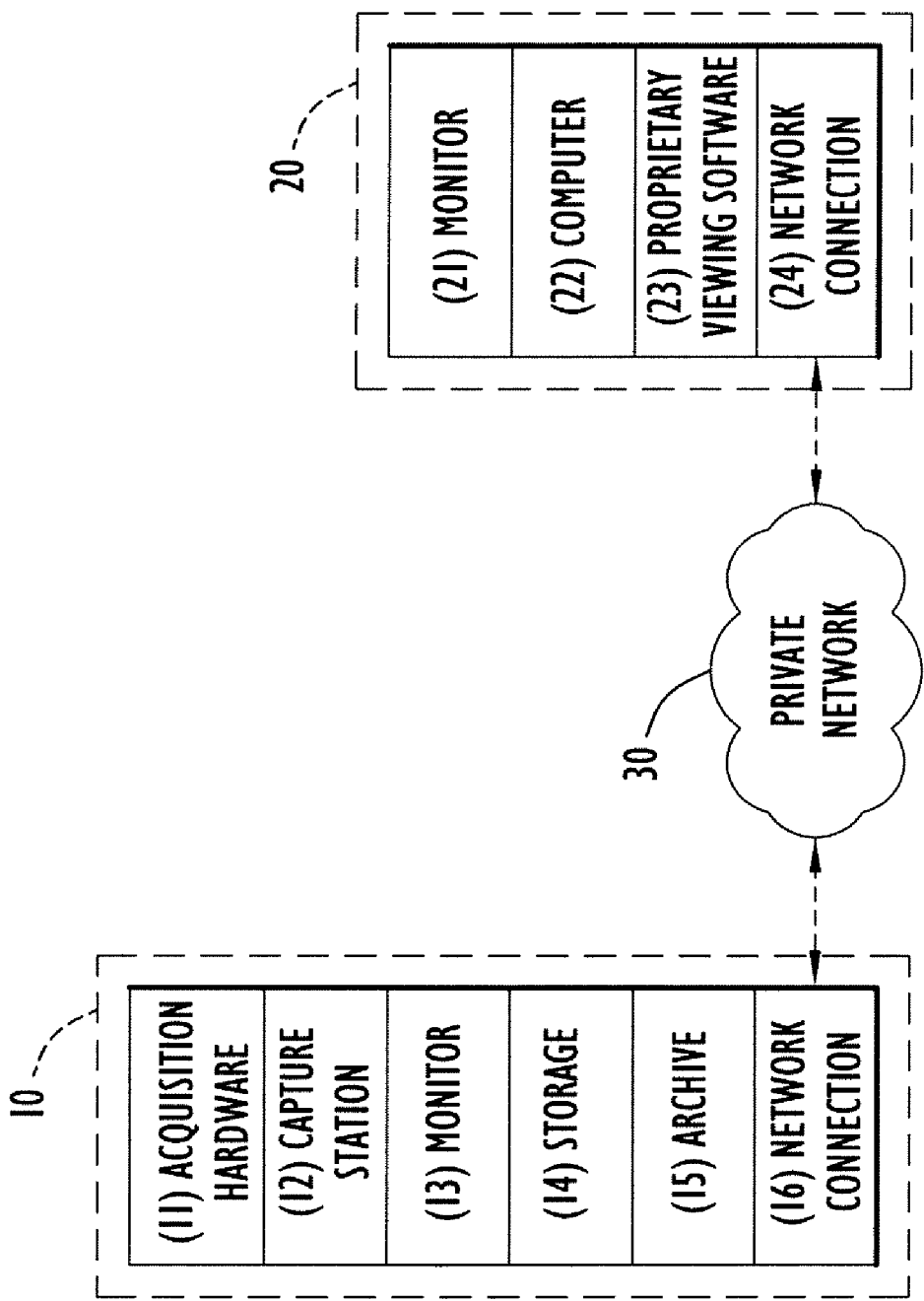
FIG. 1 is a diagrammatic illustration of a conventional ophthalmology modality environment.
Figure 2:
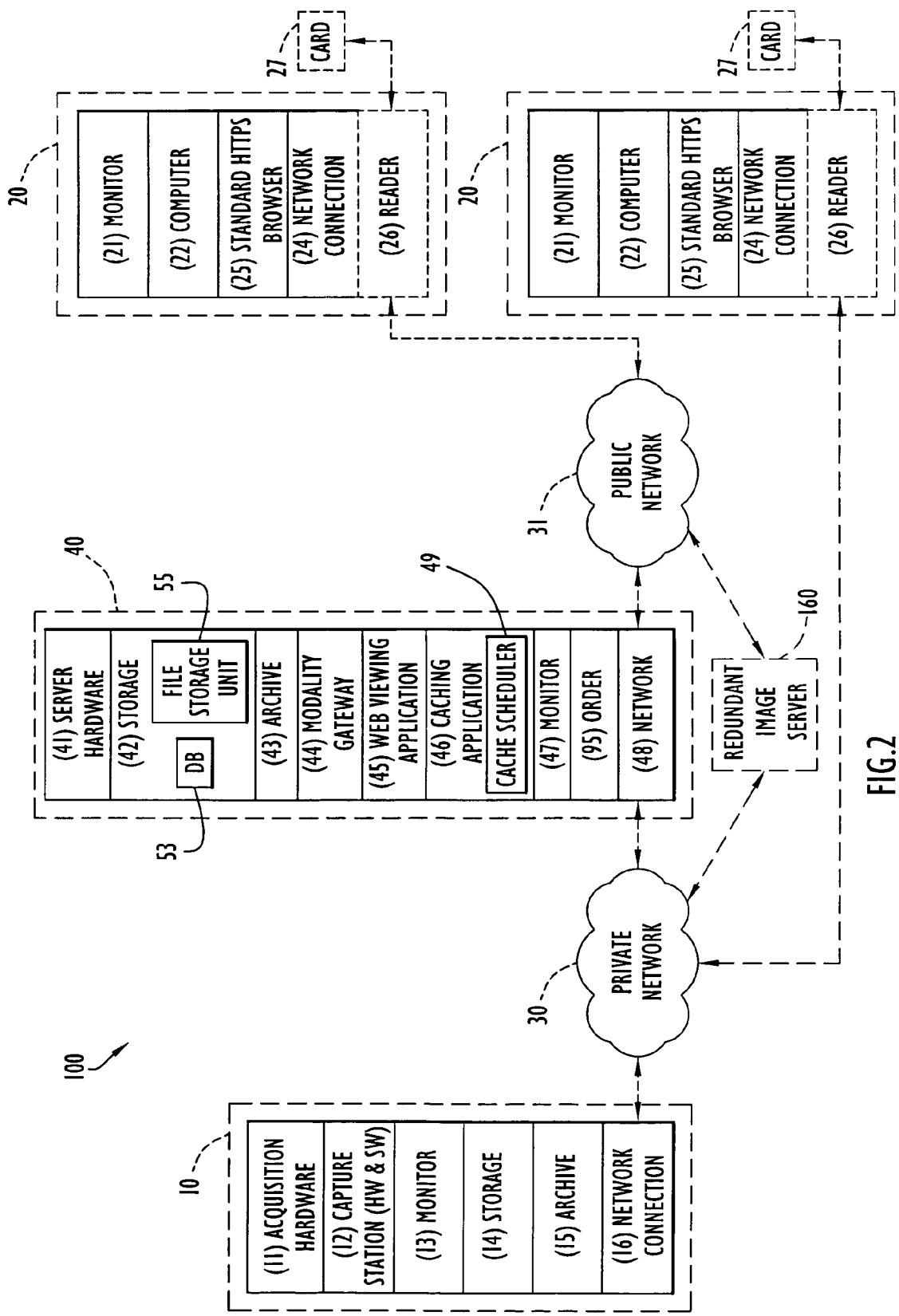
FIG. 2 is a diagrammatic illustration of an ophthalmology modality system according to the present invention.

The ophthalmology system according to the present invention is illustrated in FIG. 2. Specifically, system 100 includes at least one modality 10, one or more viewing stations 20, and an image server 40. The system may further include a redundant image server 160. The modalities are substantially similar to the modality described above for FIG. 1. The viewing stations are substantially similar to the viewing station described for FIG. 1, except that proprietary viewing software 23 is replaced by a conventional browser 25 and network connection 24 may facilitate communications across private and/or public networks as described below. The image server includes server hardware 41, a storage system 42, an archiving system 43, modality gateway 44, a web viewing application 45, a caching application 46, a monitor 47 and network connection 48. Server hardware 41 includes a computer and operating system upon which the ophthalmology specific applications are executed (e.g., gateway 44, web viewing application 45, caching application 46, etc.). By way of example only, the computer system may be implemented by a Dell PE 2600 computer system including a Windows 2000 Server operating system and a SQL Server 2000 database management system.

Storage system 42 stores patient study data including patient demographics and images obtained by capture station 12 of modalities 10. The storage system includes a database 53 and a file storage unit 55. The database and file storage unit may be implemented by any conventional or other types of storage devices. The file storage unit stores the patient study data, while the database stores information to validate and track the information within the file storage unit. In particular, a code is generated for each image file imported into or received by the image server based on the image data. The code may be generated by any conventional or other technique (e.g., checksum, MD5 hash code, etc.). The code is stored within the database and associated with the corresponding image stored within the file storage unit. Since the images are stored separate from the codes, the database may have a reduced size. The code is used to validate the images displayed on a web page or screen. Basically, a code is generated from the data of the image for display and compared to the code of the original image stored within the database, where matching codes indicate a valid image. The codes enable detection of changes to images subsequent storage of the image in the system. By way of example, when a proofsheet is opened (e.g., FIGS. 9-12), the system validates the images by comparing the codes generated for the displayed images to the codes of the original images stored in the database. An error message may be displayed to notify the user of an invalid image.

Archiving system 43 allows data stored in storage system 42 to be backed-up and removed from the location in order to recover the data if a disaster or catastrophic event occurs. The archiving system may be implemented by any conventional or other storage system and may perform various types of storage back-up. For example, the archiving system may perform a back-up of database 53, of database 53 and images from capture stations in compressed form within file storage unit 55, or of database 53 and original and compressed images within file storage unit 55. The type of back-up performed depends on the storage capacity of archiving system 43 and the desired reliability. For example, back-up of the original images provides maximum reliability and recovery of those images, but requires additional storage capacity due to the large size of the original image file. Back-up of the compressed image files provides reduced reliability and recovery of lost original images relative to back-up of the original image files, but requires less storage capacity.

Modality gateway 44 automatically collects study information (e.g., patient demographics and images) from each of the connected modalities 10. Web viewing application 45 provides a user interface for, and secure authenticated access to, the patient demographics and images/videos. The user interface of web viewing application 45 basically emulates the manner in which fast film based study analysis is performed. The security aspects of web viewing application 45 include encrypting data sent to users, maintaining which patient was seen by each user, maintaining which users have seen each patient, providing a global user login where users can view all patients, providing a limited user login where users can only view their own patients and/or providing a student user login where users can only view teaching cases without patient demographics. Basically, each user may be provided with certain access rights to control the information viewed by that user. For example, the user may view all examinations, be limited to the patients associated with the user, or be limited to any desired portions of the information (e.g., teaching cases without demographic information, etc.).

Caching application 46 predicts which patient data will be required by viewing stations 20 and moves that data proactively to the viewing stations as described below. Monitor 47 allows the system to be configured and maintained. The monitor checks for system problems (e.g., processor performance, disk space and memory utilization of system components (e.g., viewing station, image server, gateway units (FIGS. 4A-4B), etc.), database availability, image server availability, external gateway unit functionality, disruption of connections or power, network faults, etc.) and reports (e.g., via electronic mail, etc.) detected conditions to remote operation centers. The monitor may be configured to monitor, detect and report any desired system conditions.

Network connection 48 enables communications with each of the modalities and viewing stations via private network 30 and/or public network 31. In addition, the image server may include an order module 95 to enable ophthalmologists or other users to order examinations for patients. In this case, the system may provide a web page or screen enabling the ophthalmologist to define the particular test or examination desired. The information may be entered in various fashions (e.g., checkboxes for predetermined criteria, text box for entry of text, menus, etc.). The system forwards the entered information to a technician at a capture station to generate the desired images. The resulting images are provided to the system in the manner described below, where the ophthalmologist may view the examination images, typically within minutes. The components of the image server are preferably implemented by any conventional or other units performing the functions described above, where the units may include any hardware and/or software modules to accomplish those functions.

Redundant image server 160 is substantially similar to image server 40 described above and is employed for fault tolerance to assume the functions of image server 40 in response to an image server failure. The redundant image server is coupled to the various system components (e.g., modality 10, image server 40, viewing stations 20, etc.) via private network 30 and public network 31. The redundant image server receives periodic updates from image server 40 for storage system 42 to enable the redundant server to include sufficient information to replace the image server in response to a failure. By way of example, the data within the redundant server lags the data within the image server by approximately fifteen minutes. This provides a reduced initialization for the redundant server since that server should include a majority of the required information (e.g., commonly referred to as a "warm" system). However, the data within the redundant server may be updated at any desired intervals.

Figure 3:
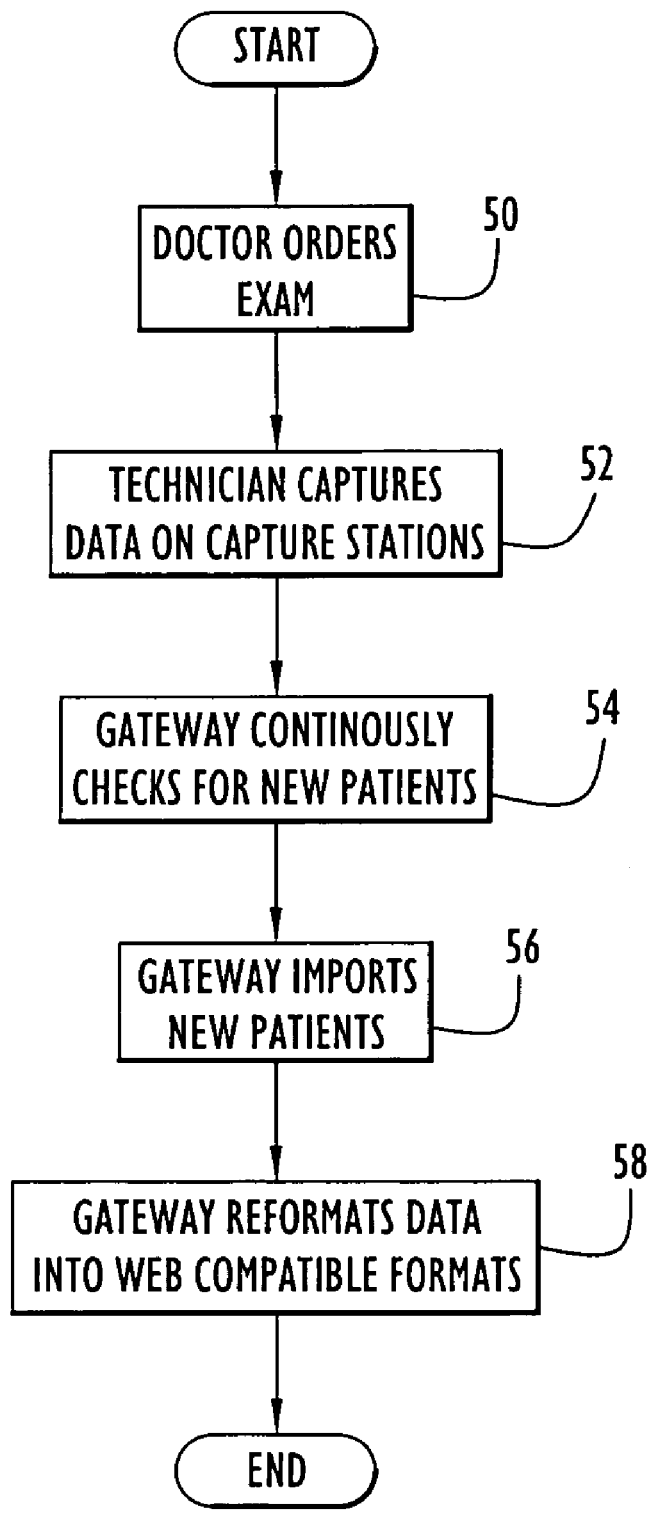
FIG. 3 is a procedural flow chart illustrating the manner in which the present invention system retrieves and processes patient images from modality capture stations.

The manner in which the image server retrieves and processes information from modalities 10 is illustrated in FIG. 3. Specifically, an ophthalmologist or other medical personnel orders an examination for a patient at step 50. A technician or modality operator enters patient data into a modality database of capture station 12 (FIG. 2) and captures modality specific images or videos of the patient for storage in modality storage subsystem 14 at step 52.

Modality gateway 44 continuously checks for the presence of new patient data in modalities 10 at step 54 and imports the new patient data to image server 40 via private network 30 at step 56. Unlike radiology and other fields, where standards exist for transmitting patient study information, ophthalmology modalities store patient studies in proprietary formats and do not automatically deliver studies to a central location. Thus, medical gateway applications are generally designed for compatibility with a single or particular capture station or interface, where the gateway is passive and has data sent to the gateway via that interface. Modality gateway 44 of the present invention is designed to be universal and is compatible with several capture stations. The modality gateway understands the proprietary formats of each modality 10, automatically retrieves the information (e.g., patient data, images, videos, raw data and processed analysis) from the modalities and stores the information in image server 40, maintains the proprietary measurement parameters of each modality and associates the parameters with each study.

In particular, the present invention modality gateway includes a plurality of interface applications each compatible with a particular capture station. Modality gateway 44 selects the appropriate interface application for a modality to actively retrieve patient data from that modality. The interface applications are designed to navigate the capture station and interface to retrieve the appropriate patient data from the capture station. Alternatively, the present invention may employ a client application on the capture station. This is effectively a software button or switch that enables or notifies modality gateway 44 to access the capture station in response to a technician or medical personnel generating new patient image and/or other data.

The patient data or records generated within the capture station are associated with a patient identifier, while patient examinations are associated with an examination identifier and linked to the patient via the patient identifier. The images acquired by the capture station are associated with patient examinations based on the examination identifier and are typically stored in files within directory folders. The capture station further maintains a time stamp (e.g., time and/or date) of when a record associated with a patient (e.g., patient data record, image, etc.) has been generated or modified. The modality gateway inspects the time stamp information to determine the presence of any new or modified patient data. The inspection may be performed in a polling fashion (e.g., every time interval) or in response to the software button or switch as described above. In particular, each patient may be associated with one or more examinations with each examination associated with one or more images. The patients, examinations and images are linked via the patient and examination identifiers as described above. If new or modified patient data is present, the modality gateway retrieves the new or modified information and stores the information in the image server. Basically, the modality gateway utilizes the patient identifier to determine the examinations associated with a patient. Once the examinations are determined, the identifier of an examination is used to retrieve the associated images. Thus, the modality gateway can navigate the capture station to retrieve the desired patient information.

Modality gateway 44 reformats the images retrieved from the capture station at step 58 to web compatible formats to enable users to view the images via the user interface provided by web viewing application 45 as described below.

Since the image files may be quite large (e.g., 100-500 megabytes), the modality gateway basically compresses the images for enhanced transmission over public network 31 to the viewing stations. The modality gateway may employ any conventional compression techniques (e.g., images may be compressed up to sixty times (where the ratio is configurable), lossless compression techniques and compression ratios of three to one may be applied for large files, etc.) and may produce any desired web compatible file formats (e.g., JPEG, PDF, etc.).

Figure 4A:
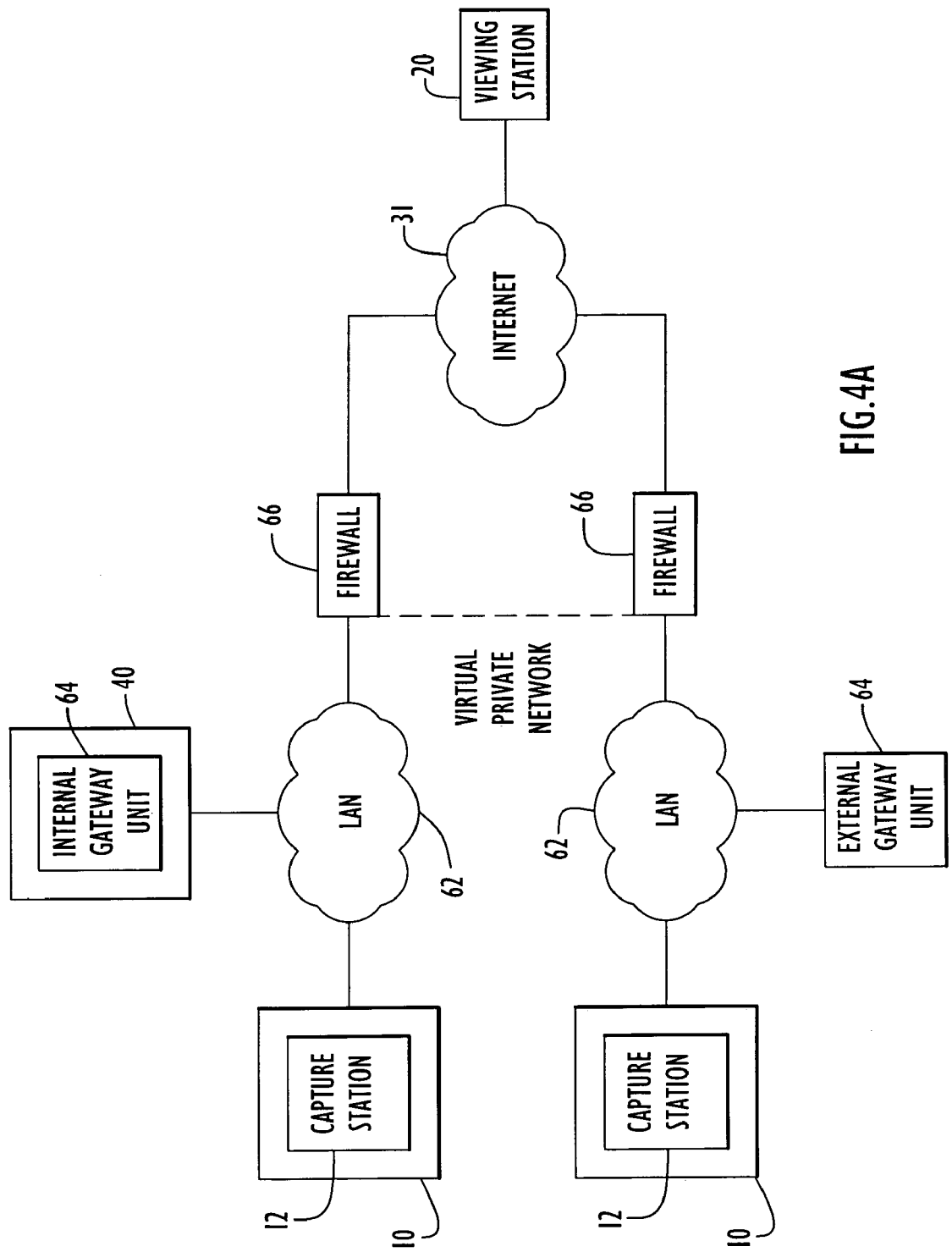
FIG. 4A is a diagrammatic illustration of a network topology according to the present invention including individual gateways for transferring patient image files.

The present invention system may alternatively employ modality gateway 44 as a stand-alone or individual unit to enhance transference of patient information from modalities 10 to image server 40 as illustrated in FIG. 4A. Specifically, an exemplary configuration includes modalities 10 each with a corresponding capture station 12, local area networks (LAN) 62, firewalls 66, public network 31 (e.g., Internet), image server 40 and an external gateway unit 64. Modalities 10 are as described above with each being coupled to a corresponding local area network 62. The local area networks are each coupled to public network 31 via a corresponding firewall 66. The firewalls effectively form a virtual private network (VPN). Image server 40 is coupled to one of the local area networks for communications with the public network and transference of information with a corresponding capture station 12. Image server 40 is substantially similar to the image server described above and includes an internal gateway unit 64.

External gateway unit 64 is coupled to the other local area network for communications with the public network and transference of information with a corresponding capture station 12. The internal gateway unit is preferably implemented as a software module or application on the image server, while the external gateway is typically implemented by a processing device including hardware and/or software. The internal and external gateway units are similar in function to modality gateway 44 described above and enhance transmission of information from the capture stations to image server 40 as described below. Viewing station 20 is substantially similar to the viewing station described above and is coupled to public network 31 to facilitate communications with and receive images from image server 40 for display.

Generally, image files produced by capture stations 12 are quite large (e.g., 100-500 megabytes). Since the transmission rate across the public network tends to be low (e.g., 1.5 megabits per second), transferring the large original image files across the network requires a substantial time interval and may significantly increase network traffic. Further, the substantial transference time interval delays the availability of patient information upon generation at the capture station.

In order to enhance transmission of the image files and provide availability of patient information, the present invention employs external gateway unit 64 in communication with a capture station 12 via local area network 62. Since the transmission rate across the local area network (e.g., 10/100/1000 megabits per second) is significantly greater than that of the public network (e.g., 1.5 megabits per second), the external gateway unit retrieves the large original image file and other patient information from the capture station. This is typically accomplished via polling or in response to the software button or switch in substantially the same manner described above. The external gateway unit formats and compresses the original image file for web application 45 (FIG. 2) as described above for transmission across the public network to image server 40. The gateway unit may employ any conventional compression techniques to produce any desired file formats (e.g., ZIP, JPEG, PDF, etc.) and may generate one or more compressed images having varying resolutions and/or sizes. The gateway unit transmits the compressed image file (s) and patient information to the image server via public network 31, thereby enabling a user at viewing station 20 to access and view the compressed image and patient information almost immediately after generation. Although the compressed image may have lower quality than the original image, the quality is sufficient for medical personnel to perform analysis, while patient information generated at the capture station is available almost immediately due to the reduced transmission time of a compressed file (e.g., two to three seconds for a T1 line).

The external gateway unit further transmits the original formatted image file to the image server for access by the viewing station. The quality of the original image is preferable, especially for performing various patient evaluations and diagnoses based on the patient image. The external gateway unit schedules the original formatted image file for transmission at a time typically set to time intervals of low user network utilization and traffic in order to enhance the transfer time of the large image file. Thus, users may view patient information almost immediately after generation while the large image files are transferred at low network utilization times, thereby conserving network bandwidth and minimizing effects on network traffic. The internal gateway unit of image server 40 may perform functions similar to those of the external gateway unit for transference of information to other image servers or viewing stations.

Caching application 46 (FIG. 2) may similarly enhance transmission of the images to the viewing stations. The caching application employs heuristics to determine where the images retrieved from a modality should be proactively positioned to reduce image loading times at viewing station 20. In other words, the caching application predicts the particular viewing stations likely to request the image and forwards the image to locations local to those stations in anticipation of the request. In this fashion, the image is pre-stored at a location local to the viewing station prior to an actual request for that image, thereby significantly reducing the time for displaying the image at the viewing station. The caching heuristics may include various techniques (e.g., most-recently-generated, past-user-patterns, similar-patient-names, same-patient-id, etc.).

Figure 4B:
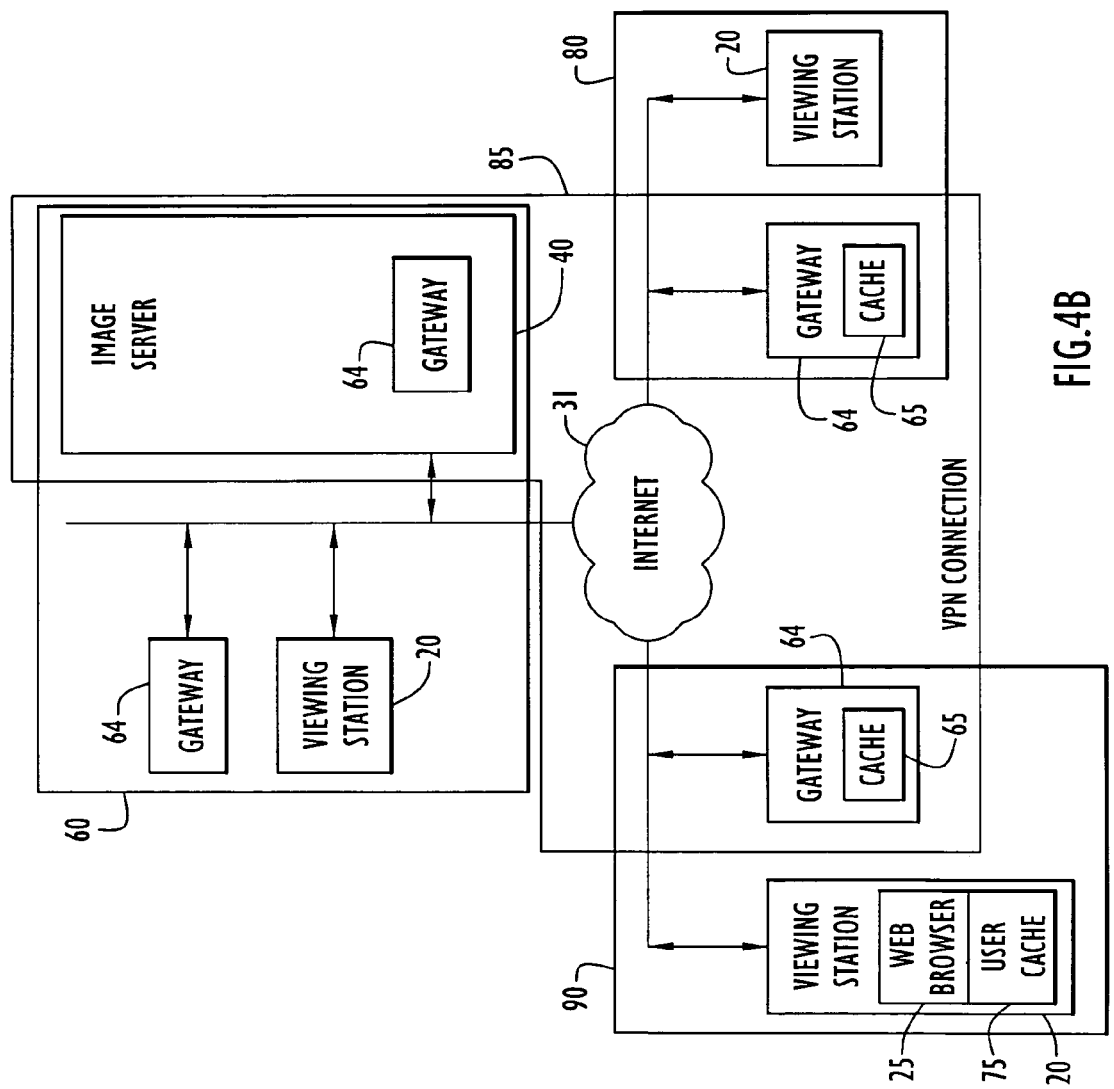
FIG. 4B is a diagrammatic illustration of an exemplary topology according to the present invention including individual gateways for caching and transference of patient image files.

An exemplary topology employing cashing and individual gateways to enhance transference of information from remote locations according to the present invention is illustrated in FIG. 4B. Specifically, an exemplary configuration includes remote sites 60, 80 and 90 in communication via public network 31 (e.g., Internet). Remote site 60 includes image server 40, an external gateway unit 64 and a viewing station 20 each coupled to the other and to public network 31. Image server 40 is substantially similar to the image server described above and includes an internal gateway unit 64. The internal gateway unit is preferably implemented as a software module or application on the image server as described above. The internal and external gateway units are similar in function to modality gateway 44 and/or caching application 46 described above and enhance transmission of information between the capture stations, image server and viewing stations as described below. The external gateway is coupled to a corresponding capture station or modality (not shown) to transfer images as described below and is typically implemented by a processing device including hardware and/or software. Viewing station 20 is substantially similar to the viewing station described above and facilitates communications with and receives images from image server 40 for display as described below.

Remote site 80 includes an external gateway unit 64 and a viewing station 20 each coupled to the other and to public network 31. The external gateway unit is coupled to a corresponding capture station or modality (not shown) to transfer images as described below. External gateway unit 64 includes a cache memory 65 to store images received from the corresponding capture station for transference to image server 40 and/or viewing stations 20 as described below. The external gateway unit is similar in function to modality gateway 44 and/or caching application 46 described above and enhances transmission of information between the capture stations, image server and viewing stations as described below. The external gateway is typically implemented by a processing device including hardware and/or software, while viewing station 20 is substantially similar to the viewing station described above and facilitates communications with and receives images from image server 40 and/or the external gateway unit for display as described below.

Remote site 90 includes an external gateway unit 64 and plural viewing stations 20 each coupled to the other and to public network 31. The external gateway unit is coupled to a corresponding capture station or modality (not shown) to transfer images as described below. The external gateway unit includes a cache memory 65 to store images received from a corresponding capture station for transference to viewing stations 20 as described below. The external gateway unit is similar in function to modality gateway 44 and/or caching application 46 described above and enhances transmission of information between the capture stations, image server and viewing stations as described below. Viewing stations 20 are substantially similar to the viewing station described above and facilitate communications with and receive images from image server 40 and/or the external gateway unit for display as described below. A viewing station 20 of remote site 90 further includes a user cache 75 to store images for display by that viewing station as described below. Image server 40 and external gateway units of remote sites 80, 90 are coupled via a virtual private network 85 to ensure secure communication of image information.

Generally, image files produced by capture stations 12 are quite large (e.g., 100-500 megabytes). Since the transmission rate across the public network tends to be low (e.g., 1.5 megabits per second), transferring the large original image files across the network requires a substantial time interval and may significantly increase network traffic. Further, the substantial transference time interval delays the availability of patient information upon generation at the capture station. In addition, a hospital has many remote clinic sites that generate digital images of examinations with relatively narrow public network bandwidth. Since the external gateway units of remote sites 80, 90 transfer image files to the image server at remote location 60 via the private network connection over public network 31, the bandwidth to access images remotely from the viewing stations is limited, thereby increasing the time for viewing stations to display images at the clinic or other remote sites.

In order to enhance transmission of the image files and provide availability of patient information, the present invention provides the external gateway units of remote sites 80, 90 with cache memory 65. The cache memory is expandable and typically includes a certain amount of storage space (e.g., in the range of sixty to two-hundred fifty gigabytes) to store compressed images that are accessible to local users at respective sites 80, 90. This enables the user to retrieve and view the images from the cache memory of the local gateway unit to avoid additional traffic between the image server and that remote location. The image server further detects the user login location to redirect an image request from that user to the proper cache memory (e.g., remote clinic location, public location, image server location (e.g., may be the same as the public location), etc.), typically local to the requesting user. Cache memory 65 of the external gateway units primarily stores compressed and thumbnail images (e.g., approximately six months to one years worth of image files) and may store a limited amount of original images (e.g., a few days worth of images).

Initially, the external gateway units of remote sites 80, 90 retrieve the large original image file and other patient information from corresponding capture stations. This is typically accomplished via polling or in response to the software button or switch in substantially the same manner described above. The external gateway units format and compress the original image files for web application 45 (FIG. 2) as described above. The gateway units may employ any conventional compression techniques to produce any desired file formats (e.g., ZIP, JPEG, PDF, etc.) and may generate one or more compressed or other image versions having varying resolutions and/or sizes (e.g., thumbnail images, etc.). The compressed images are stored in corresponding cache memory 65, while the original and compressed images are transmitted from the external gateway units to image server 40 via virtual private network 85. The large original image files may be transmitted to the image server at times of low network utilization (e.g., at night, etc.) to reduce network traffic. The external gateway units continue to store new compressed images in accordance with the memory storage capacity. Although the compressed images may have lower quality than the original image, the quality is sufficient for medical personnel to perform analysis, while patient information generated at the capture station is available almost immediately. Original images are generally not stored in the cache memory due to the large file size that impedes delivery through the public or private network. These files are primarily stored on the image server. An external gateway unit may store recent original images within a certain date range; however, the amount of storage is limited by the capacity of the hard disk or disk array of that unit. The storage capacity of the remote gateway unit is configurable in order to store the maximum quantity of files for high efficiency.

The images stored within cache memories 65 of the external gateway units are utilized to respond to requests from users local to those cache memories at remote sites 80, 90. In particular, image requests from viewing stations 20 of remote sites 80, 90 are transmitted to image server 40. The image server determines the IP address (e.g., client IP address) of each requesting user and includes information pertaining to pre-configured zones of IP groups. The IP address for a requesting user is compared to the zone information to determine the zone of that requesting user. The zone address is typically the same as the address of the external gateway unit at the remote location of the requesting user.

The image server determines the location of the requested image (e.g., original, compressed, thumbnail, etc.) relative to the requesting user. This determination is based on the zone of the user as described above. If the image is stored in cache memory 65 of an external gateway unit local to the requesting user, the screen or web page is generated by the image server with the image being retrieved from the local gateway unit. When the local gateway unit does not contain the requested image, the image server generates the screen or web page with the image being retrieved from the image server storage. Basically, the image server (e.g., web viewing application 45) provides the web page or screen (e.g., XML or HTML code)

to the user or viewing station web browser with a pointer (e.g., URL, URI, etc.) to indicate the location and enable retrieval of the requested image.

In the event an external gateway unit 64 is local to the image server or resides at remote site 60, images received by the external gateway unit from a corresponding capture station are compressed and the original and compressed images are stored directly in the image server. Viewing station 20 at remote site 60 may access the images from the image server, thereby obviating the need to redundantly store images in a gateway unit cache memory.

Alternatively, a viewing station at a remote site may include a cache memory to enable the viewing station to retrieve images from a local hard disk or memory. Since patient and examination information are stored in the local cache memory prior to requests for that information, users experience minimum delays and the fastest access time. In particular, viewing station 20 at remote site 90 includes web browser 25 and a cache memory 75. External gateway units 64 receive images from corresponding capture stations and generate versions of the image (e.g., compressed, thumbnail, etc.) having varying compressions, sizes and resolutions as described above. The resulting images are stored in the image server and gateway cache memories as described above. Caching application 46 (FIG. 2) of the image server includes a cache scheduler module 49 to monitor the stored information and copy the information (e.g., original, compressed and/or thumbnail images, etc.) from either a local gateway unit or image server storage to the viewing station cache memory. The cache scheduler module monitors newly stored information and determines the user or user group associated with that information. This may be determined based on the zones of the user and the external gateway unit providing the information. If the available capacity of the viewing station cache memory is insufficient to receive a new image, the oldest stored image is removed to enable receipt of the new image. The transfer of information to the viewing station cache memory may occur at predetermined intervals (e.g., fixed, dynamic, etc.) or in response to particular conditions (e.g., receipt of a certain quantity of images, etc.).

When the viewing station cache memory is employed, requested images (e.g., original, compressed, thumbnail, etc.) may be retrieved from either the viewing station cache memory, the local gateway unit cache memory or the image server storage. Specifically, image requests from viewing station 20 of remote site 90 are transmitted to image server 40. The image server determines the IP address (e.g., client IP address) of the user as described above. The image server determines the location of the requested image relative to the requesting user. This determination is based on the zone of the user as described above. If the image is stored in cache memory 75 of the viewing station, the screen or web page is generated by the image server with the image being retrieved from the viewing station cache memory. Otherwise, when the image resides in cache memory 65 of an external gateway unit local to the requesting user, the screen or web page is generated by the image server with the image being retrieved from the local gateway unit. If neither the viewing station nor local gateway unit contains the requested image, the image server generates the screen or web page with the image being retrieved from the image server storage. Basically, the image server (e.g., web viewing application 45) provides the web page or screen (e.g., XML or HTML code) to the user or viewing station web browser with a pointer (e.g., URL, URI, etc.) to indicate the location and enable retrieval of the requested image.

This topology further enables newly generated images to be accessed with minimal delay since images from capture stations are compressed and accessible from gateway units (e.g., obviating the need to transmit large original images to the image server for access). Further, the requested image is retrieved from the location nearest the viewing station or user. For example, a search for an original image requested by a local user is initially conducted within the viewing station and/or local gateway unit cache, and subsequently within the image server storage (e.g., primary, backup and redundant storage), while the image search for a user remote from gateway units is conducted in the image server storage (e.g., primary, backup and redundant storage). A search for a compressed or thumbnail image requested by a local user is initially conducted within the viewing station and/or local gateway unit cache, and subsequently within the image server storage (e.g. primary storage). In the case of the user being remote from the external gateway unit, there is no need to search and the image is retrieved from the image server since compressed and thumbnail images have reduced transmission times relative to original images (e.g., due to their reduced sizes) and are transmitted to the image server as described above.

The manner in which a user operates the present invention to view patient information is illustrated in FIGS. 5-20. Initially, web viewing application 45 (FIG. 2) of image server 40 provides the interface for a user in the form of screens or web pages (FIGS. 6-20) for security and viewing of information as described below. Specifically, an ophthalmologist or other medical personnel logs securely into image server 40 (FIG. 2) at step 70 via a viewing station 20 using web browser 25 and a login screen or web page 110 (FIG. 6). A User ID and password are entered on the login screen in corresponding fields 112 and a login button 114 is actuated (e.g., clicked on by a mouse) to log into the image server. The system (e.g., web viewing application 45) maintains information pertaining to each session. By way of example, the system may store the users accessing or logging in to the system, the time of the access or login, the patients viewed and any other desired information as described above.

Screen 110 includes a link menu 105 disposed toward the top of the screen. The link menu includes links pertaining to Login, Study, Patient and Log Out. The Login link enables display of login page or screen 110 to log into the system. The Study link enables display of an examination list screen or web page 115 (FIG. 7) that lists the study examinations, while the Patient link enables display of a patient list screen or web page 200 (FIG. 15) to create and import examination records. The Log Out link enables a user to log out of the system. In order to completely log out, the Log Out link is actuated to display a logout screen or web page including a Complete Logout button. If this button is not actuated, the user can still access the system. Further, if the system is idle for a predetermined time interval, the system automatically logs the user out completely. The default timeout interval is configurable and, by way of example only, is typically set to thirty minutes.

Alternatively, system 100 may detect the presence of ophthalmologists near a viewing station to provide automatic login and patient data retrieval functions. In particular, viewing station 20 of system 100 (FIG. 2) may further include a reader 26. The reader communicates with or receives signals from a wireless transmission card 27 that is maintained by an ophthalmologist or other medical personnel. The wireless card and reader may be implemented by any conventional or other wireless transceivers, receivers and/or transmitting devices. The wireless transmission card may be worn or held and is typically maintained on a user's person. The wireless transmission card stores and transmits login and other information to reader 26. The reader receives the information and transfers information to computer system 22 for processing. This enables the viewing station to detect the presence of ophthalmologists at the remote location of a viewing station. Computer system 22 may utilize the information to automatically log the detected ophthalmologist into image server 40 and display screens containing information associated with patients of the detected ophthalmologist as described below.

Further, the ophthalmologist location may be transmitted to image server 40 to enable the image server to perform caching functions as described above. Basically, since the image server is aware of the locations of ophthalmologists, newly generated or other image data associated with patients of the ophthalmologists may be transmitted to locations local to the corresponding viewing stations prior to and in anticipation of requests for that data from the viewing stations. This enhances the response time of the viewing stations since requested images have already been transferred to the local locations.

Once the ophthalmologist is logged into the image server, the ophthalmologist is presented with examination list screen 115 (FIG. 7) including link menu 105 as described above and a customized list of studies of interest. Each user may be provided with certain access rights to control the information viewed by that user as described above. For example, the list may include (or the user may be limited to) the patients associated with the user, thereby obviating or reducing the need to perform a search. Further, the list may include (or the user may be permitted to view) all examinations or any desired portions thereof (e.g., teaching cases without demographic information, etc.). Screen 115 serves as the default screen and is displayed when a user first gains access to the system or when the Study link within link menu 105 is actuated from a system screen.

Screen 115 shows patient examination's in the form of a table and listed by the examination date. Each table row provides information indicated by the table columns for a corresponding examination. By way of example only, the table columns include Select, Record ID, Last Name, First Name, Gen, Birth Date, Exam Date, CS, View?, Cmp?, V?, R?, Doctor, Proc, Pathology or Diagnosis, Tcase and Imported. The Select column includes an icon that enables selection of a patient and display of a patient history screen or web page 120 (FIG. 8) in response to clicking on or actuating the icon. Screen 120 lists all examinations associated with the selected patient. The Record ID column indicates a Modality Patient ID generated by a specific capture station 12 or any other record generator. The Last and First name columns indicate the name of the patient, while the Gen column indicates the patient's gender. The Birth and Exam Date columns respectively indicate the birth date of the patient and date of examination. The CS column indicates the modality type used for this exam (e.g. MRP, OCT3, TOPCON, IMPORT, etc.).

Figure 9:
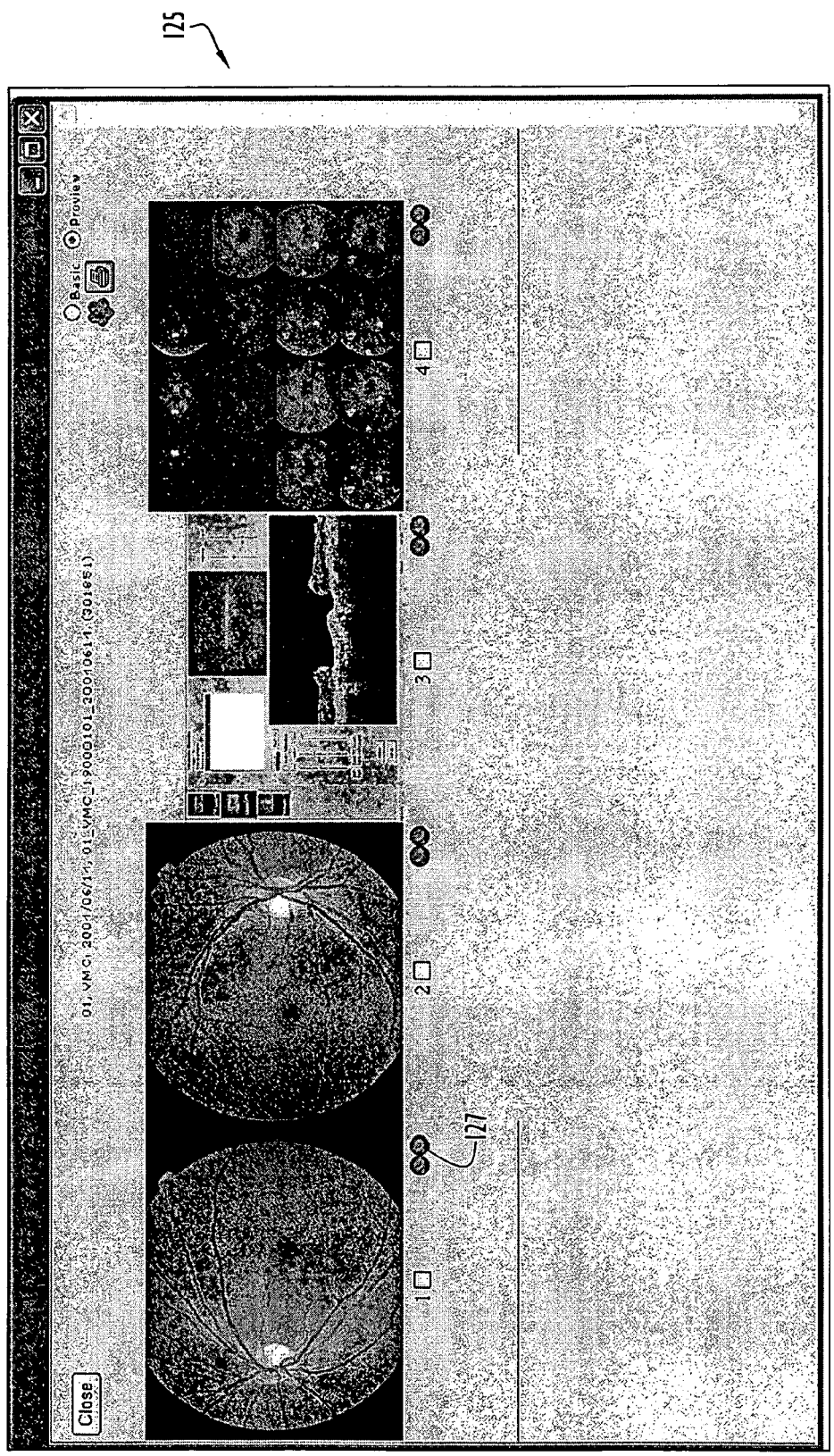
FIG. 9 is an illustration of an exemplary graphical user screen employed by the present invention to display a proofsheet.
Figure 10:
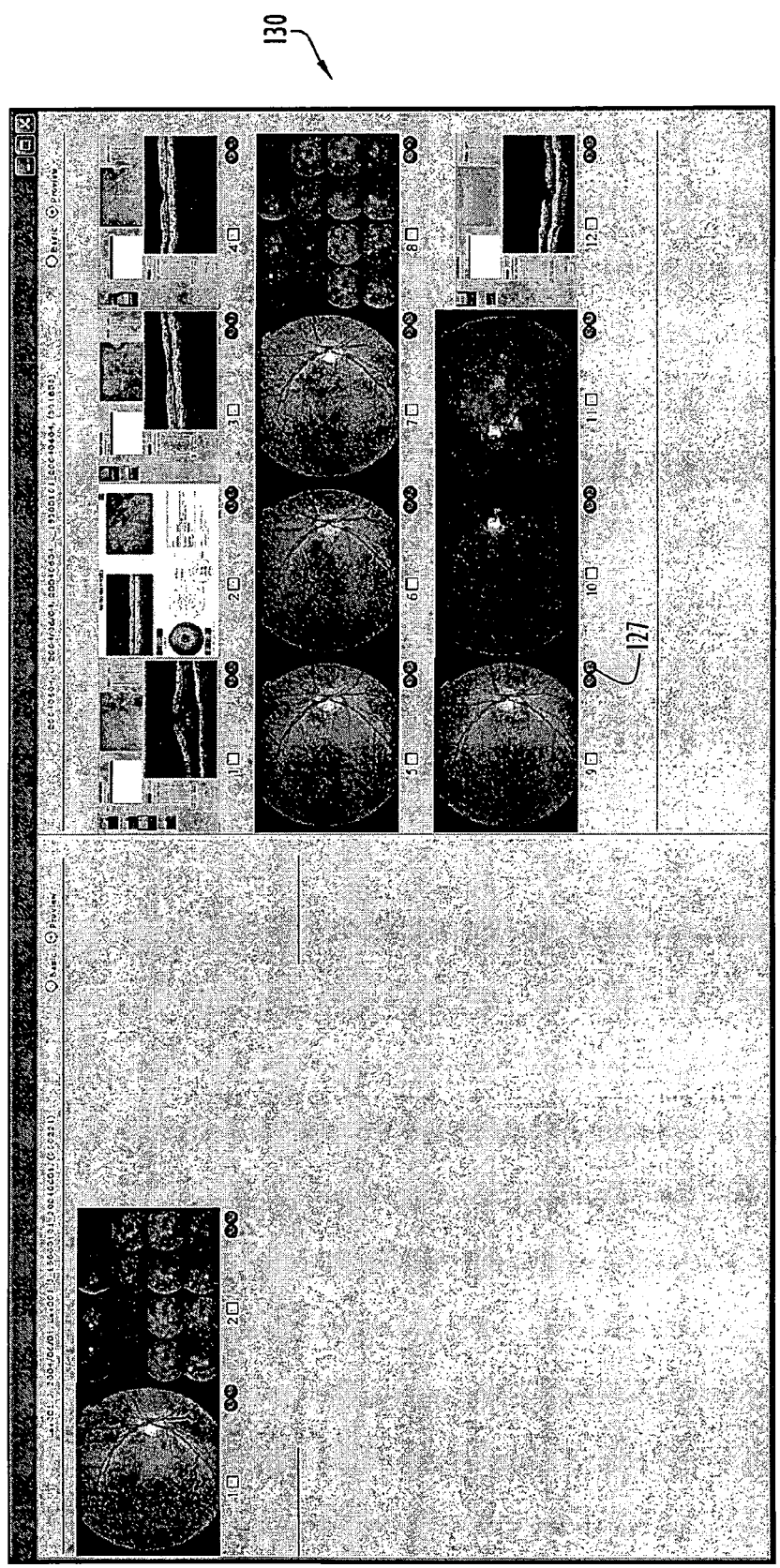
FIG. 10 is an illustration of an exemplary graphical user screen employed by the present invention for displaying a comparison proofsheet.
Figure 11:
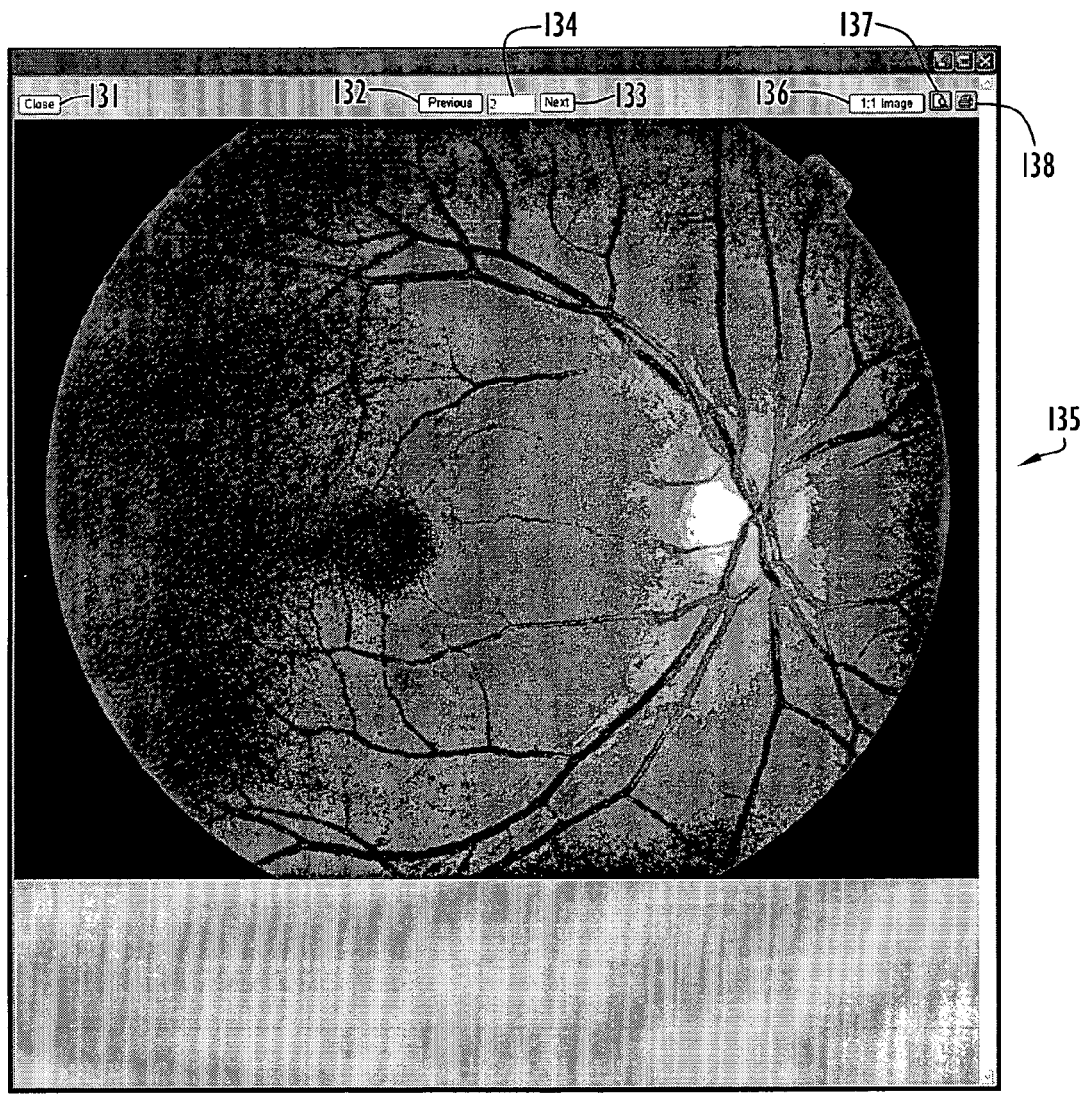
FIG. 11 is an illustration of an exemplary graphical user screen employed by the present invention for displaying a basic detailed image.

The View? Column includes icons that enable display of an examination proofsheet image (FIG. 9). If images exist for the corresponding patient or examination, one or more icons appear in the View? column. The CMP? column includes checkboxes that enable selection of two examination proofsheets for comparison. The checkboxes are alternately selected and deselected by clicking on those checkboxes. When a second proofsheet is selected, two examination proofsheets are displayed for study comparison (FIG. 10).

The V? column includes icons (e.g., check mark and question mark) to indicate verification of a corresponding examination image. This column is primarily utilized by the technician or photographer generating the image to verify that the examination image has been imported correctly. By way of example only, a verified examination is indicated by a green check mark icon in the V? column, while an unverified examination is indicated by a red question mark. The examination verification icons can be set or toggled only by a user with a user identification matching that of the person who originally loaded or verified the image (e.g., technician or photographer). If the examination image is already verified and a corresponding examination record is updated (e.g., more image files have been imported into the same examination record), the verified icon (e.g., green check mark) is changed to an unverified icon (e.g., red check mark). In this case, the original user (e.g., technician or photographer) needs to re-verify the examination record.

The R? column is similar to the V? column and includes icons (e.g., check mark and question mark) to indicate review of a corresponding examination image. This column is primarily utilized by an ophthalmologist to indicate that the examination image has been reviewed. By way of example only, a reviewed examination is indicated by a green check mark icon in the R? column, while an examination that has not been reviewed is indicated by a red question mark. The examination review icons can be set by an initial reviewer, but subsequently toggled only by a user with a user identification matching that of the person who originally reviewed the image. If the examination image is already reviewed and a corresponding examination record is updated (e.g., more image files have been imported into the same examination record), the reviewed icon (e.g., green check mark) is changed (e.g., to a red check mark) to indicate the updated images have not been reviewed. In this case, the user originally reviewing the image needs to review the examination record.

The Doctor column indicates the name of the patient's doctor, while the Proc column indicates the procedure type for this examination (e.g. Color, Fluorescein, Visual Fields, Ultrasound, etc.). The Pathology column indicates the diagnosis of a patient (e.g. Glaucoma, Choroidal Folds, Macular Pucker, etc.). This field can be modified under the patient history screen (FIG. 8) as described below. The Tcase column indicates whether the corresponding patient or examination is a testing case and can be set under the patient history screen (FIG. 8) as described below. The Imported column indicates the date of importation. In addition, the table may further include a SYS ID column that indicates a system generated identifier for a corresponding examination and/or an Rproc column including an icon that enables reprocessing of the image due to changes from the capture station. In this case, the images need to be reprocessed and recompressed.

Figure 13A:
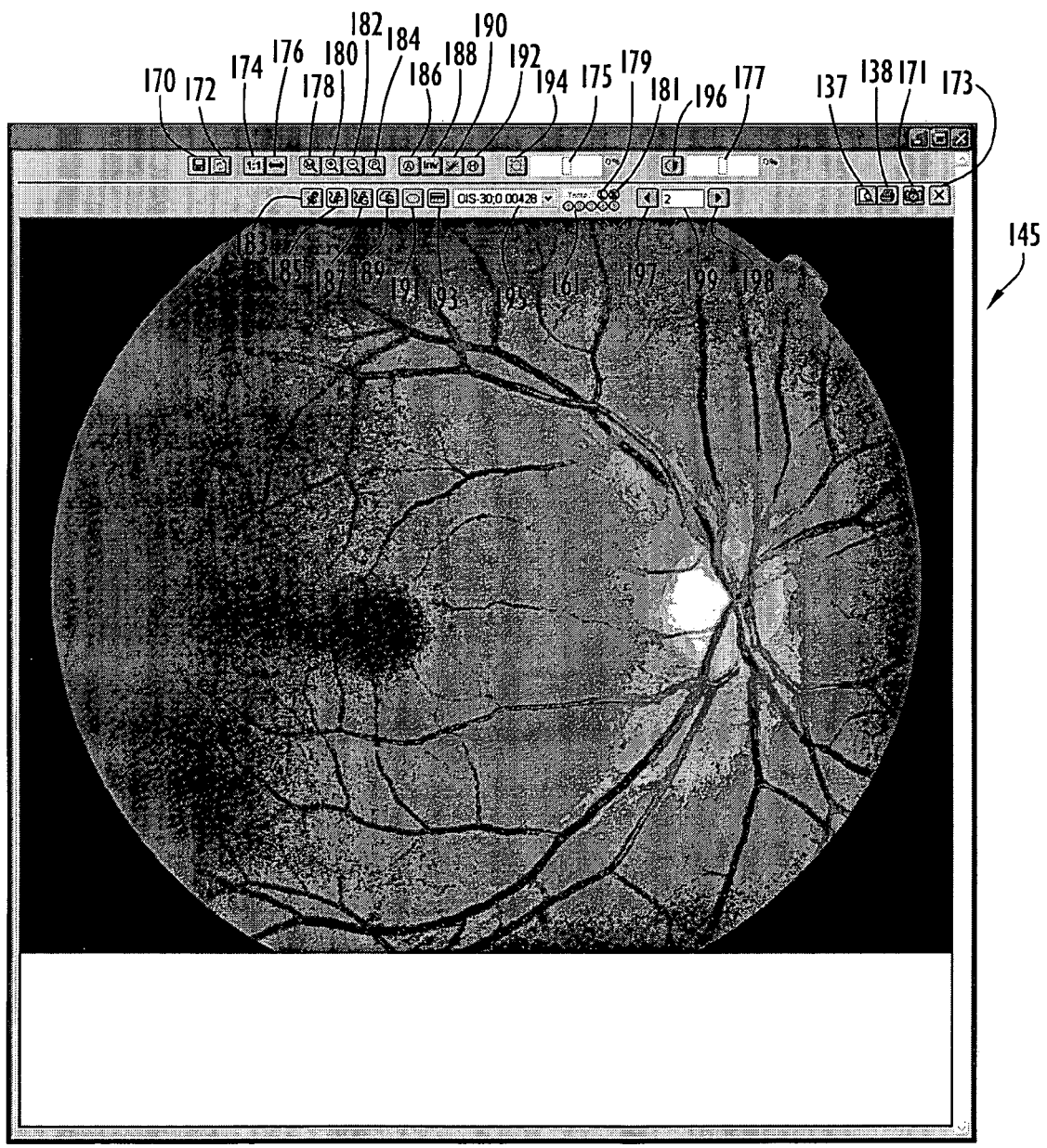
FIGS. 13A-13B are illustrations of an exemplary graphical user screen employed by the present invention for displaying a manipulable detailed image.
Figure 13B:
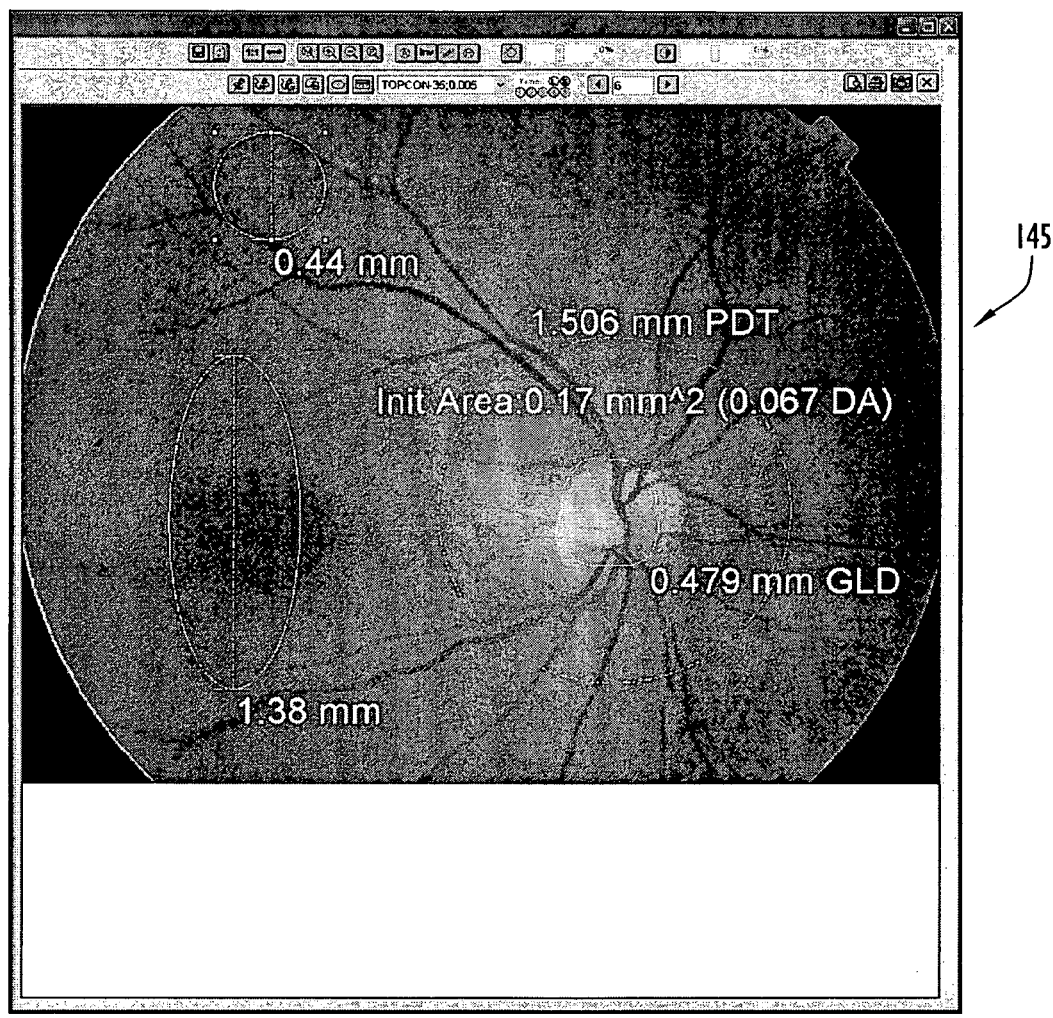
Figure 14:
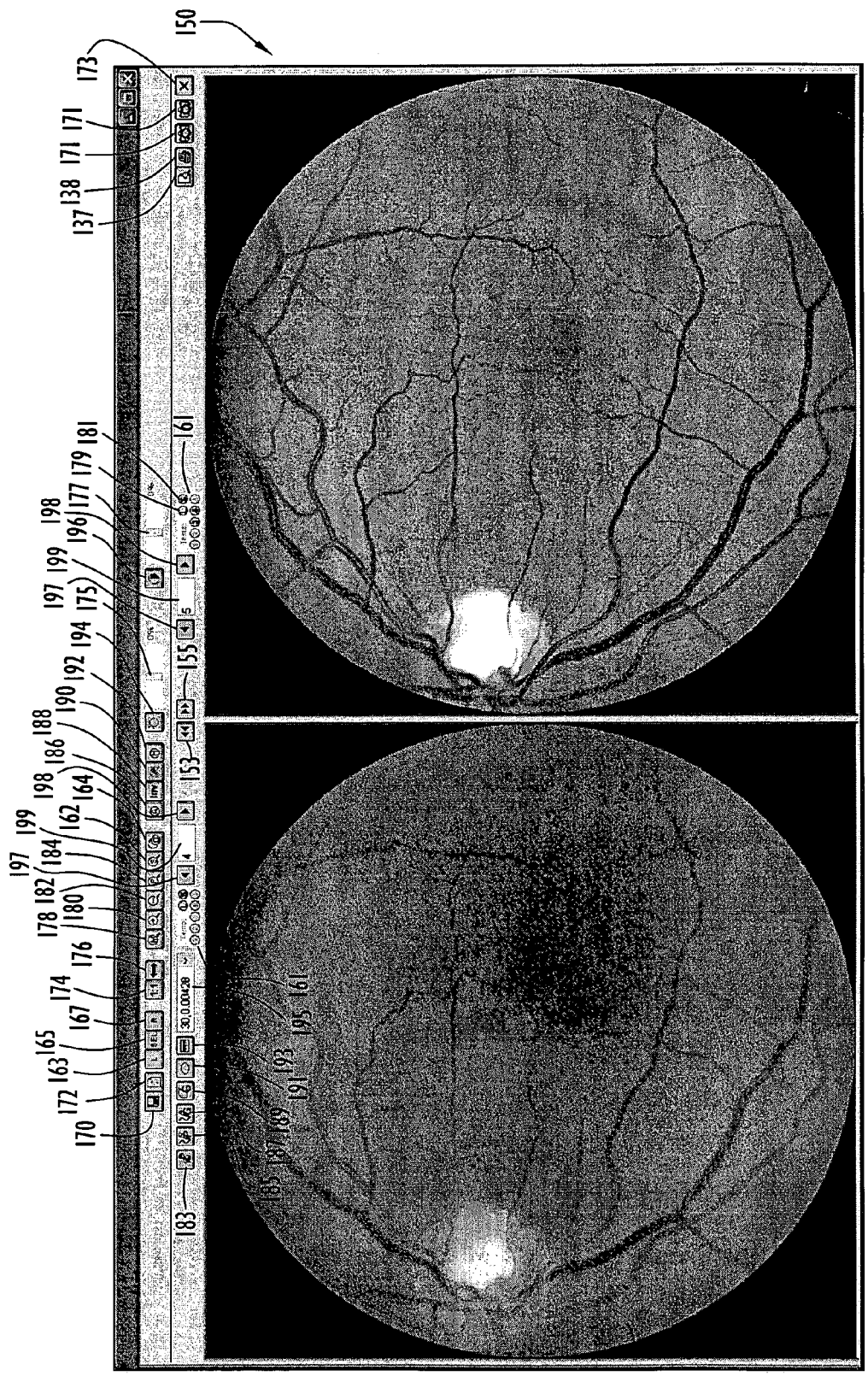
FIG. 14 is an illustration of an exemplary graphical user screen employed by the present invention for displaying a pair of manipulable images.

Screen 115 further includes a download Proview button 117 that enables additional features in image view screens (e.g., FIGS. 13A-13B and 14). This setting enables a user to manipulate images locally on browser 25 (FIG. 2) for brightness and contrast, zooming, one-to-one image view, panning, auto intensity, annotations, measurement tools as well as other features for the images. In order to provide the proview setting, proview images must be downloaded from this page; otherwise, only a basic view is available.

The table within screen 115 enables an ophthalmologist to search for specific studies, review studies, compare studies, perform diagnostic analysis, and save the analysis. In particular, a search may be performed based on date or based on a category and corresponding value. Screen 115 includes a Today button 116, a Last Seven Day button 118, an All button 119 and a From button 320. Today button 116 and From button 320 enable the system to retrieve all examinations with the current date (or date of system use) or from a date, while Last Seven Day button 118 retrieves all examinations taken in the last seven days. The All button enables retrieval of all examinations in the system.

A search may further be performed based on a category and corresponding value. Screen 115 includes a drop-down list 111 containing the various categories and a corresponding field 113 to receive a category value. By way of example only, the categories include: All Patients to display all examinations (e.g., values entered in the corresponding field are ignored); Patient Name (First and/or Last name) to search based on a patient's name using just first name, just last name or both first and last names (e.g., the name does not have to be completely spelled out, where the system searches for the patient's name that contains the field value); Doctor (First and/or Last name) to search based on the doctor's name using just first name, just last name or both first and last names (e.g., the name does not have to be completely spelled out, where the system searches for the doctor's name that contains the field value); Exam Procedure to search based on a procedure type for an examination (e.g. Color, Fluorescein, etc.), where the system searches for the procedure with the exact match; Pathology to search based on the diagnosis of a patient (e.g. Glaucoma, Choroidal Folds, Macular Pucker, etc.), where the system searches for pathology descriptions that contain the field value; Modality Patient ID (Record ID) to search based on a Modality Patient ID generated by a specific capture station or other record generator, where the system searches for the ID that contains the field value; System Patient ID to search based on the system generated system ID for the particular examination, where the system searches for the ID with the exact match; Modality (e.g., MRP, OCT3, TOPCON, IMPORT, etc.) to search based on the modality type used for the examination (e.g. MRP, OCT3, TOPCON, IMPORT, etc.), where the system searches for the modality with the exact match; and Teaching Case Only to search based on the indication of a testing case (e.g., where values entered in the corresponding field are ignored). When a search category and value are entered, date search buttons 116, 118 or 119 are further actuated to perform a search based on category and/or date.

Once the desired examination list is displayed, the list or table may be sorted by any item that includes a sort button icon 109 (e.g., Record ID, Last Name, First Name, Gen, Birth Date, Exam Date, CS, Doctor, Proc, Pathology, Tcase and Imported). The sort is alternately performed in descending and ascending order in response to successive icon actuations.

Screen 115 further includes page-setting features. By way of example only, these features include: a Total Records field that indicates the number of total records/examinations retrieved; a Records Per Page field that enables control of the quantity of records per page to be displayed (e.g., if this setting is changed, an icon needs to be actuated to apply the new setting); a Show Previous Page icon 101 to enable advancement to a previous page of the examination list; a Show Next Page icon 102 to enable advancement to the next page of the examination list; a Show First Page icon 103 to enable advancement to the first page of the examination list; and a Show Last Page icon 104 to enable advancement to the last page of the examination list. The screen may further include an X of Y indication to indicate the page number displayed relative to the number of pages available.

Once screen 115 is displayed to the ophthalmologist, a particular patient and/or examination may be selected via actuation of the appropriate icons at step 72 (FIG. 5) as described above. If the ophthalmologist selects one or more examinations via the View? and/or CMP? column icons, the appropriate images are displayed (e.g., FIGS. 9-14) for analysis as described below for step 74. When the ophthalmologist selects a particular patient via the Select column icon, the system displays patient history screen 120 (FIG. 8) with link menu 105 as described above and a listing of examinations associated with a selected patient. Navigation back to examination list screen 115 may be accomplished by clicking on Back button 122 or by clicking on the Study link within link menu 105.

Screen 120 lists all records for the selected patient with the most recent examination being listed first. The selected patient's last and first names and date of birth are displayed on the top of the page. The patient examinations are displayed in the form of a table and listed by the examination date. Each table row provides information indicated by the table columns for a corresponding examination. By way of example only, the table columns include Record ID, Middle Name, Gen, Exam/Import, CS, View?, Procedure, Pathology, Tcase and Note. The Record ID column indicates a Modality Patient ID generated by a specific capture station 12 or any other record generator. The Middle Name column indicates the middle name of the patient, while the Gen column indicates the patient's gender. The Exam/Import column indicates the examination date. If the examination is imported as described below, the import date is further displayed and is indicated in a different color, preferably blue. The CS column indicates the modality type used for this examination (e.g. MRP, OCT3, TOPCON, IMPORT, etc.).

The View? Column includes icons that enable display of an examination proofsheet image (FIG. 9). If images exist for the corresponding patient or examination, one or more icons appear in the View? column. If an icon is clicked, the particular proofsheet is displayed, while checkboxes are utilized to view plural proofsheets. The checkboxes are alternately selected and deselected by clicking on those checkboxes. When a second proofsheet is selected, two examination proofsheets are displayed for study comparison (FIG. 10).

The Proc column indicates the procedure type for this examination (e.g. Color, Fluorescein, Visual Fields, Ultrasound, etc.), while the Pathology column indicates the diagnosis of a patient (e.g. Glaucoma, Choroidal Folds, Macular Pucker, etc.). The Tcase column indicates whether the corresponding patient or examination is a testing case, and the Note column includes notes for the patient. The individual entries within the Pathology, Tcase and Note columns can be modified via screen 120. In particular, each of these columns includes an update button 123 associated with each entry in that column. When an entry has been modified, actuation of the corresponding update button facilitates storage of the modified entry. In the case of the Tcase column, the update button serves as a switch to enable or disable the teaching case status and icon.

Once patient history screen 120 is displayed, the ophthalmologist may select patient images for viewing. Actuating or clicking on an icon within the View? column enables display of one or more images pertaining to the corresponding examination. Actuating or clicking on checkboxes within the View? column enables the study of comparison images. Depending on the setting, the system may, by way of example, display either two or four examination images to compare. However, the system may display a maximum of six examination images. Screen 120 includes a two studies comparison icon or button 124 and a four studies comparison icon or button 126. The two studies comparison icon enables comparison of two examination images and permits only two checkboxes within the View? column to be selected. When this is set, icon 124 is in color; otherwise the icon is gray. The four studies comparison icon enables display of multiple examination proofsheet images and permits a maximum of four checkboxes to be selected. When this icon is set, the icon is in color; otherwise the icon is gray. The multiple proofsheets are displayed vertically with images for each proofsheet extending horizontally in time order.

Once the ophthalmologist has selected the desired examinations, the corresponding images are displayed for analysis by the ophthalmologist at step 74 (FIG. 5), where analysis results may be saved and/or printed at step 76. In particular, when a View? column icon is actuated or clicked on examination list screen 115 (FIG. 7) or patient history screen 120 (FIG. 8), an individual proofsheet window 125 (FIG. 9) is displayed. If Cmp? column checkboxes on examination list screen 115 (FIG. 7) or the View? column checkboxes on patient history screen 120 (FIG. 8) are selected, a proofsheet for a study comparison window 130 (FIG. 10) is displayed. The individual and study comparison proofsheet windows include similar features and enable viewing of particular images as described below.

The proofsheet windows 125, 130 (FIGS. 9-10) include the patient information displayed at the top of the page. This information typically includes the patient last and first names, examination date and image filename. The proofsheet windows further include various images and information pertaining to the selected patients and/or examinations that may be individually viewed. Basically, there are two settings for viewing an image. The basic view has minimal features and enables "scrolling" through images. This view includes a one-to-one image viewing feature. Images are displayed in the basic view unless Proview images are downloaded from examination list screen 115 as described above. Images may be stored to a user computer or to any other application (e.g. Microsoft PowerPoint program, etc.) from the basic view proofsheets and from the basic image view windows (e.g., via click-and-drag, right-click and "save as", etc.).

The Proview setting displays Proview or manipulable images (FIGS. 9 and 10). This setting provides numerous features including adjustment for brightness and contrasts, zooming, one-to-one image view, panning, auto intensity, annotations, measurement tools for single images, etc. These features are enabled by downloading Proview images from examination list screen 115 as described above.

Figure 12:
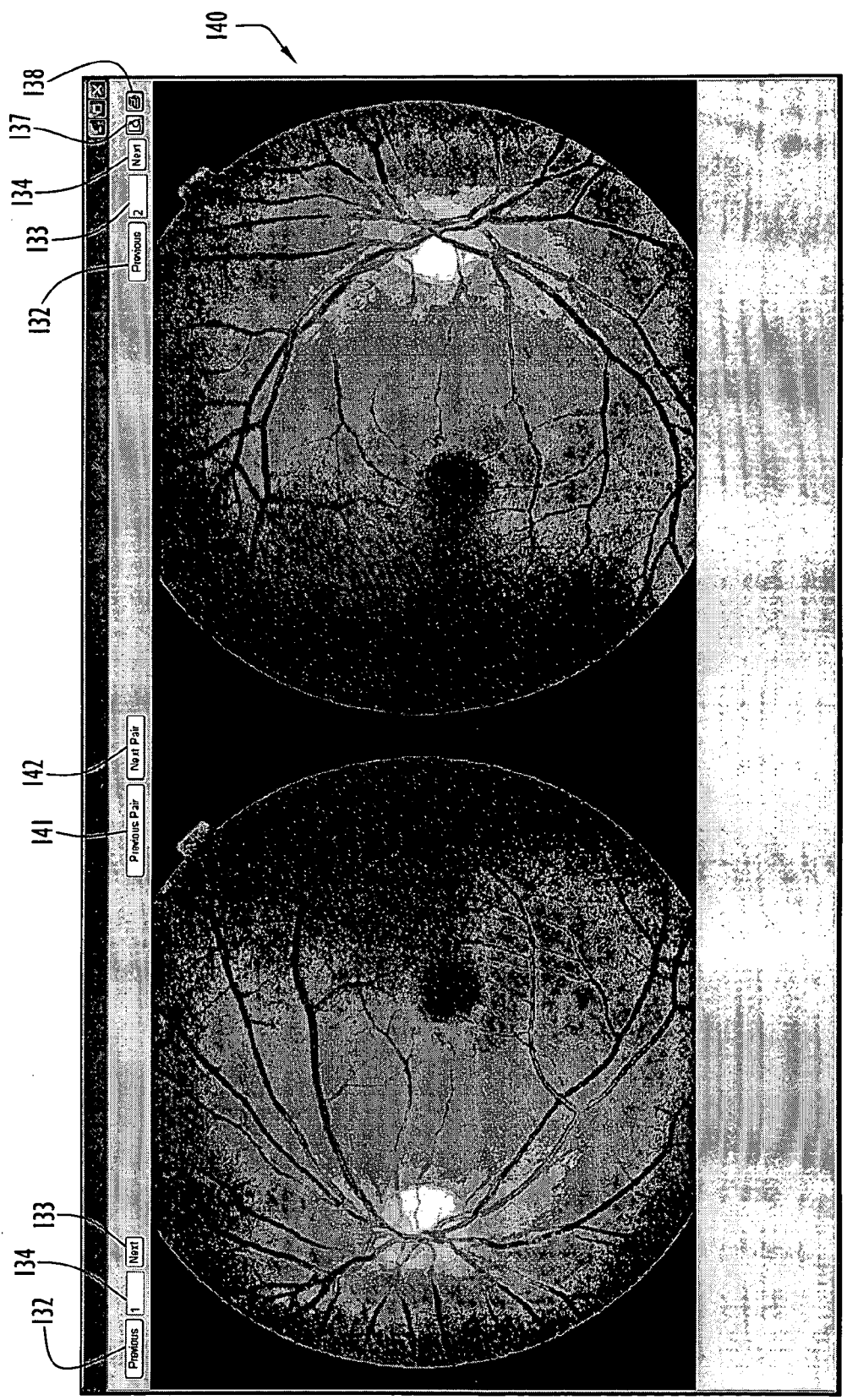
FIG. 12 is an illustration of an exemplary graphical user screen employed by the present invention for displaying a basic detailed pair of images.

A single image window 135 (FIG. 11), 145 (FIG. 13A) is displayed in response to clicking on an image within the proofsheet windows (FIGS. 9-10). A pair image window 140 (FIG. 12), 150 (FIG. 14) may be displayed by selecting checkboxes on the proofsheet windows (FIGS. 9-10) that are each associated with a displayed image. When a second checkbox or image is selected, a new window 140, 150 with the two selected images (FIGS. 12 and 14) is displayed for comparison. Alternatively, the proofsheet windows include stereo image icons 127 that enable display of a window 140, 150 containing a pair of consecutive images associated with the actuated stereo image icon (FIGS. 12 and 14). For example, the stereo image icon enables display of corresponding consecutive images from the proofsheet (e.g., image numbers one and two from the proofsheet, image numbers two and three from the proofsheet, etc.).

A single image window may include a basic view (e.g., window 135 of FIG. 11) or a Proview or manipulable view (e.g., window 145 of FIG. 13A). Similarly, a pair image window may include a basic view (e.g., window 140 of FIG. 12) or Proview or manipulable view (e.g., window 150 of FIG. 14). The single image and pair image windows provide the basic features unless Proview images have been downloaded as described above. The single image and pair image windows for the respective basic and Proview images have similar features as described below.

A single image basic view window 135 (FIG. 11) includes the displayed image. The basic setting enables a user to click-and-drag the individual image to a desktop of a computer or viewing station (e.g., via right-click and "save as", etc.) or to any other application (e.g. Microsoft PowerPoint program, etc.). Window 135 further includes a close icon or button 131, a previous image button or icon 132, a next image button or icon 133, a current image number field 134, a view actual size icon or button 136, a print preview icon or button 137 and a print icon or button 138. The close window button enables closure of window 135. Previous image button 132 enables display of a previous image from the proofsheet, where the system wraps from the first image to the last image. Next image button 133 enables display of the next image from the proofsheet, where the system wraps from the last image to the first image. Clicking on the displayed image also enables display of the next image. Current image number field 134 indicates the image of the proofsheet currently being displayed on the window. View 1:1 Image button 136 maps each pixel on the screen to one pixel on the original image. The 1:1 image is shown in a new window. Print preview button 137 enables the print format of the image to be previewed before printing, while print button 138 enables printing of the displayed image and/or window.

A pair image basic view window 140 (FIG. 12) includes a pair of images displayed adjacent each other. Window 140 further includes a previous image button or icon 132 for each image, a next image button or icon 133 for each image, a current image number field 134 for each image, a previous pair button or icon 141, a next pair icon or button 142, print preview icon or button 137 and print icon or button 138. Previous image button 132 enables display of a corresponding previous image from the proofsheet (e.g., independent of the other displayed image), where the system wraps from the first image to the last image. Next image button 133 enables display of a corresponding next image from the proofsheet (e.g., independent of the other displayed image), where the system wraps from the last image to the first image. Clicking on the displayed image also enables display of the next image. The current image number field indicates for a corresponding image the image from the proofsheet currently being displayed on the window.

Previous pair button 141 enables display of a previous pair of images from the proofsheet when the images are displayed in response to the stereo image icon, where the system wraps from a first pair to the last pair of images. Clicking on the left-hand side image (e.g., as viewed in FIG. 12) also displays a previous pair of images from the proofsheet. For example, if window 140 is displaying image numbers six and seven of the proofsheet, the previous pair images are image numbers four and five. Next pair button 142 enables display of a next pair of images from the proofsheet when the images are displayed in response to the stereo image icon, where the system wraps from the last pair of images to the first pair of images. Clicking on the right-hand side image (e.g., as viewed in FIG. 12) also displays a next pair of images from the proofsheet. For example, if window 140 is displaying image numbers eight and nine of the proofsheet, the next pair images are image numbers ten and eleven. Print preview button 137 enables the print format of the image to be previewed before printing as described above, while print button 138 enables printing of the displayed image and/or window as described above.

A single image proview window 145 (FIG. 13A) includes the displayed image and a series of icons or buttons to manipulate the displayed image. In particular, a save image button 170 enables storage of image and/or annotation files on the user computer and/or image server, while a refresh image button 172 refreshes or re-displays the image. A view actual size button 174 enlarges the image to map each pixel on the screen to one pixel on the original image. This button further displays a small window, where a click-and-drag operation of a square in the small window (pan window) moves the 1:1 image to a desired location. A fit to window size button 176 fits the image to the current window size. A view magnify glass button 178 magnifies a portion of the image under the magnification glass. In response to actuating or clicking on this button and moving the cursor to the image, a magnifying glass icon on the image is displayed. A click-and-drag operation may be performed to view the portion of the image magnified. Clicking on button 178 deselects the magnifying operation.

A zoom in button 180 enables zooming in to control the image view. This button displays a pan view window described below to assist in determining the image portion being viewed. A zoom out button 182 enables zooming out to control the image view. A pan control button 184 enables display of the pan view window. This window is also displayed when an image exceeds the window size. The pan view window displays a smaller version of the image to assist in determining the viewed portion. A different location of the image may be viewed in response to clicking on a different place within the pan view window. A click-and-drag operation may be performed on a square box within the pan view window to alter the view location of the image.

An auto intensity button 186 automatically adjusts the intensity, while an invert image button 188 inverts the image (e.g., dark areas are converted to white areas and white areas are converted to dark areas). A gray image button 190 changes a color image to a gray scale or black/gray/white image. A histo equalize image button 192 computes a histogram of an image (within a user-configurable range) and distributes colors equally amongst the image pixels. A brightness control button 194 controls the brightness. A brightness indicator bar 175 is positioned adjacent the brightness control button to indicate the degree of brightness. A click-and-drag operation is performed on the bar to change the brightness in terms of a percentage. Clicking on the brightness control button resets the brightness to zero percent. Once the brightness is set, the brightness is applied to each image.

A contrast control button 196 controls the amount of contrast for the image. A contrast indicator bar 177 is positioned adjacent the contrast control button. A click-and-drag operation is performed on the bar to change the contrast in terms of a percentage. Clicking on the contrast control button resets the contrast to zero percent. Once the contrast is set, the contrast is applied to each image.

An annotation toolbar 183 displays an annotation/drawing toolbar. A free-hand GLD/PDT button 185 enables a free-hand drawing for greatest linear dimension (GLD)/photo dynamic therapy (PDT). GLD and PDT are spot sizes used for analysis and treatment of various problems. GLD is the longest distance between two points of an enclosed area. PDT is a type of low intensity laser treatment combined with a photosensitive dye. The spot size for PDT is one millimeter larger than that of GLD and assists with determining an impact location for a laser. Once an area is drawn with a mouse (e.g., by a click and drag operation), the PDT and the GLD measurements and corresponding area are displayed (FIG. 13B). A free-hand GLD button 187 enables free hand drawing for GLD. Once an area is drawn with a mouse (e.g., by a click and drag operation), the GLD measurement and corresponding area are displayed. A polygon GLD button 189 enables drawing of a polygon. Clicking on the image indicates a start location of a side of the polygon, while subsequent clicks represent the point of the sides. A double-click is used to end the polygon drawing (last end of the side), where the GLD measurement and corresponding area are displayed. An ellipse button 191 enables drawing of a circle or ellipse. A click-and-drag operation is utilized to draw a circle or ellipse, where the longest dimension measurement (e.g., GLD) is displayed (FIG. 13B). Depressing a SHIFT key of a keyboard while drawing an ellipse produces a circle.

A ruler button 193 enables drawing of a straight line and display of the line measurement. The measurements described above are produced based on the quantity of pixels occupied by the measured dimension which are converted to any desired units of measurement (e.g., a millimeter includes a predetermined quantity of pixels). A measurement information field 195 is in the form of a drop down list and provides information for measurements (e.g., type of modality, degree field, the quantity of millimeters per pixel, etc.). Since capture stations provide images with different resolutions (e.g., measurement criteria or pixels per unit), the system requires a user to select an image resolution for the measurement to enhance accuracy.

A temporary annotation file load button 179 enables loading of an annotation file that was temporarily saved. This feature is performed for each user for each image. Each user can load a temporary saved annotation file per image. The annotation file includes annotations or markings for the image entered by a user. The markings are disposed on a layer that is overlaid with the image, thereby maintaining the image file in an original state. The layer including the markings or annotations is stored in the annotation file. For example, the markings described above for the measurements (FIG. 13B) may be stored in the annotation file for display with the image. The temporary annotation file may be stored on the viewing station or image server, while a permanently stored annotation file is stored on the image server for retrieval with a stored image. A temporary annotation file save button 181 enables temporary storage of an annotation file. This feature is performed for each user for each image. Each user can save a temporary annotation file per image.

Permanent annotation file icons 161 include a series of buttons to indicate the quantity of saved annotation files. The system can save a maximum of five permanent annotation files (e.g., and, hence, annotation file icon 161 includes five buttons each associated with an annotation file). Once saved, the annotation file cannot be deleted; thus the temporary annotation file save/load features are provided. When an annotation file is saved (e.g., save image button 170 is actuated to save existing temporary annotation files), a corresponding grayed out annotation button within icon 161 is colored blue to indicate a saved annotation file. Once an annotation file is loaded and displayed on the window, the blue annotation button is displayed as red. Saving a permanent annotation file also causes the corresponding thumbnail image on the proofsheet screen (FIGS. 9-10) to be marked indicating an annotation file has been saved.

A previous image button 197 enables display of a previous image from the proofsheet, where the system wraps from the first image to the last image. A current image number field 199 indicates the number from the proofsheet of the currently displayed image. A next image button 198 enables display of the next image from the proofsheet, where the system wraps from the last image to the first image. Print preview button 137 enables the print format of the image to be previewed before printing, while print button 138 enables printing of the displayed image, window and/or annotation files. A show original image button 171 enables display of the original uncompressed image, while a close window button 173 closes the window.

A pair image proview window 150 (FIG. 14) includes a pair of images displayed adjacent each other and a series of icons or buttons to manipulate the displayed images. This window has features substantially similar to single proview window 145 described above. In particular, save image button 170 enables storage of image and/or annotation files on the user computer and/or image server as described above, while refresh image button 172 refreshes or re-displays the image as described above. A select left image button 163 enables manipulations to be performed on the left image (e.g., as viewed in FIG. 14). For example, when the left image is selected and zoom in button 180 is in use, the zoom in feature is applied only to the left image. A select both images button 165 enables manipulations to be performed on both images. In other words, the features produced by the buttons of screen 150 are applied to both images. A select right image button 167 enables manipulations to be performed on the image on the right-hand side of the screen (e.g., as viewed in FIG. 14). For example, when the right-hand side image is selected and zoom in button 180 is in use, the zoom feature is applied only to the right-hand side image.

View actual size button 174 enlarges the image to map each pixel on the screen to one pixel on the original image as described above. Fit to window size button 176 fits the image to the current window size as described above. View magnify glass button 178 magnifies a portion of the image under the magnification glass as described above. Zoom in button 180 enables zooming in to control the image view. This button displays the pan view window described below to assist in determining the image portion being viewed. Zoom out button 182 enables zooming out to control the image view. Pan control button 184 enables display of dual pan view windows, each corresponding to a displayed image. These windows are also displayed when an image exceeds the window size. Each pan view window displays a smaller version of the image to assist in determining the viewed portion as described above. A different location of the image may be viewed in response to clicking on a different place within the pan view window. A click-and-drag operation may be performed on a square box within each pan view window to alter the view location of the corresponding image. If the left or right image is selected, only one pan window is displayed. A single pan button 162 enables a single synchronized pan view window to be displayed either when pan control button 184 is actuated or whenever the image exceeds the window size. The left image is displayed in the pan view window, while the window is synchronized to view two images at the same location.

An overlay button 164 enables the right image to overlay the left image. Auto intensity button 186 automatically adjusts the intensity as described above, while invert image button 188 inverts the image (e.g., dark areas are converted to white areas and white areas are converted to dark areas) as described above. Gray image button 190 changes a color image to a gray scale or black/gray/white image as described above. Histo equalize image button 192 computes a histogram of an image (within a user-configurable range) and distributes colors equally amongst the image pixels as described above. Brightness control button 194 and brightness indicator bar 175 control the brightness as described above, while contrast control button 196 and contrast indicator bar 177 control the amount of contrast for the image as described above.

An annotation toolbar 183 displays an annotation/drawing toolbar as described above. Free-hand GLD/PDT button 185 enables a free-hand drawing for GLD/PDT as described above, while free-hand GLD button 187 enables free hand drawing for GLD as described above. Polygon GLD button 189 enables drawing of a polygon as described above, while ellipse button 191 enables drawing of a circle or ellipse as described above. Ruler button 193 enables drawing of a straight line and display of the measurement in millimeters as described above. Measurement information field 195 is in the form of a drop down list and provides information for measurements (e.g., type of modality, degree field, the quantity of millimeters per pixel, etc.) as described above.

Temporary annotation file load buttons 179 are each associated with a corresponding image and enable loading of an annotation file that was temporarily saved for the corresponding image as described above. This feature is performed for each user for each image. Each user can load a temporary saved annotation file per image. Temporary annotation file save buttons 181 are each associated with a corresponding image and enable temporary storage of an annotated file for the corresponding image as described above. This feature is performed for each user for each image. Each user can save a temporary annotation file per image. Permanent annotation file icons 161 are each associated with a corresponding image and include a series of buttons to indicate the quantity of saved annotation files for the corresponding image as described above. The system can save a maximum of five permanent annotation files (e.g., and, hence, annotation file icon 161 includes five buttons) for each image as described above. Once saved, an annotation file cannot be deleted; thus the temporary annotation file save/load features are provided. When an annotation file is saved (e.g., save image button 170 is actuated to save existing temporary annotation files) for an image, a corresponding grayed out annotation button within icon 161 associated with that image is colored, preferably blue, to indicate a saved annotation file as described above. Once an annotation file is loaded and displayed on the window, the blue annotation button is displayed as red as described above. Saving a permanent annotation file also causes the corresponding thumbnail image on the proofsheet screen (FIGS. 9-10) to be marked indicating an annotation file has been saved as described above.

Previous image buttons 197 are each associated with a corresponding image and enable display of a previous image from the proofsheet with respect to the corresponding image (e.g., independent of the other currently displayed image), where the system wraps from the first image to the last image. Current image number fields 199 are each associated with a corresponding image and indicate the number from the proofsheet of the corresponding displayed image. Next image buttons 198 are each associated with a corresponding image and enable display of the next image from the proofsheet with respect to the corresponding image (e.g., independent of the other currently displayed image), where the system wraps from the last image to the first image. A previous pair button 153 enables display of a previous pair of images from the proofsheet when the images are displayed in response to the stereo image icon, where the system wraps from a first pair of images to the last pair of images. For example, if the window is displaying image numbers six and seven from the proofsheet, the previous pair images are image numbers four and five. A next pair button 155 enables display of a next pair of images from the proofsheet when the images are displayed in response to the stereo image icon, where the system wraps from the last pair of images to the first pair of images. For example, if the window is displaying image numbers eight and nine from the proofsheet, the next pair of images are image numbers ten and eleven.

Print preview button 137 enables the print format of the image to be previewed before printing as described above, while print button 138 enables printing of the displayed images, window and/or the annotation files as described above. Show original image buttons 171 are each associated with a corresponding image and enable display of the corresponding original uncompressed image as described above. Close window button 173 closes the window as described above.

Figure 5:
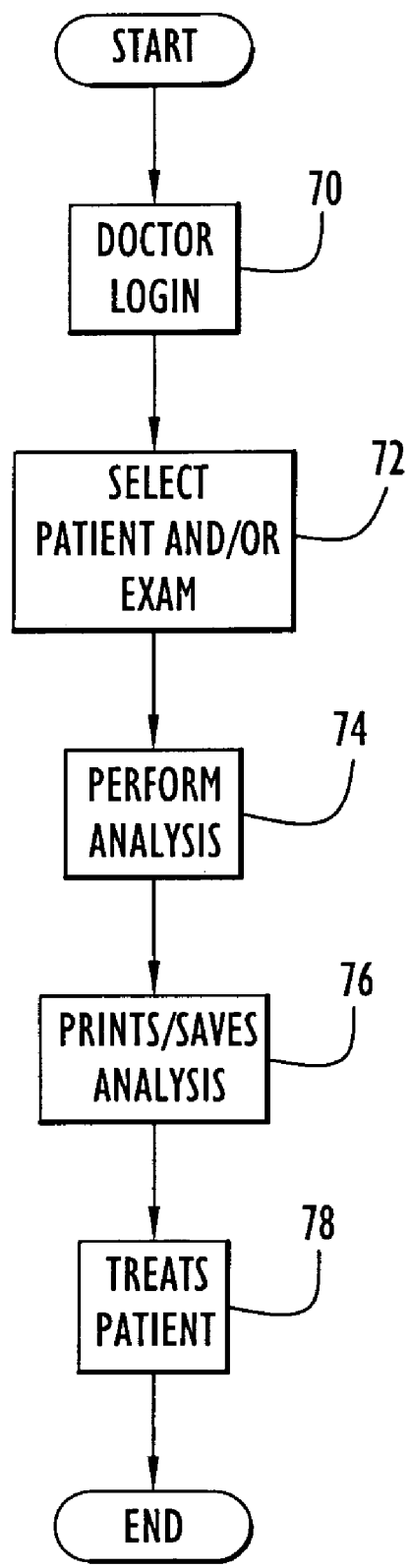
FIG. 5 is a procedural flow chart illustrating the manner in which users may retrieve and analyze patient information according to the present invention.
Figure 6:
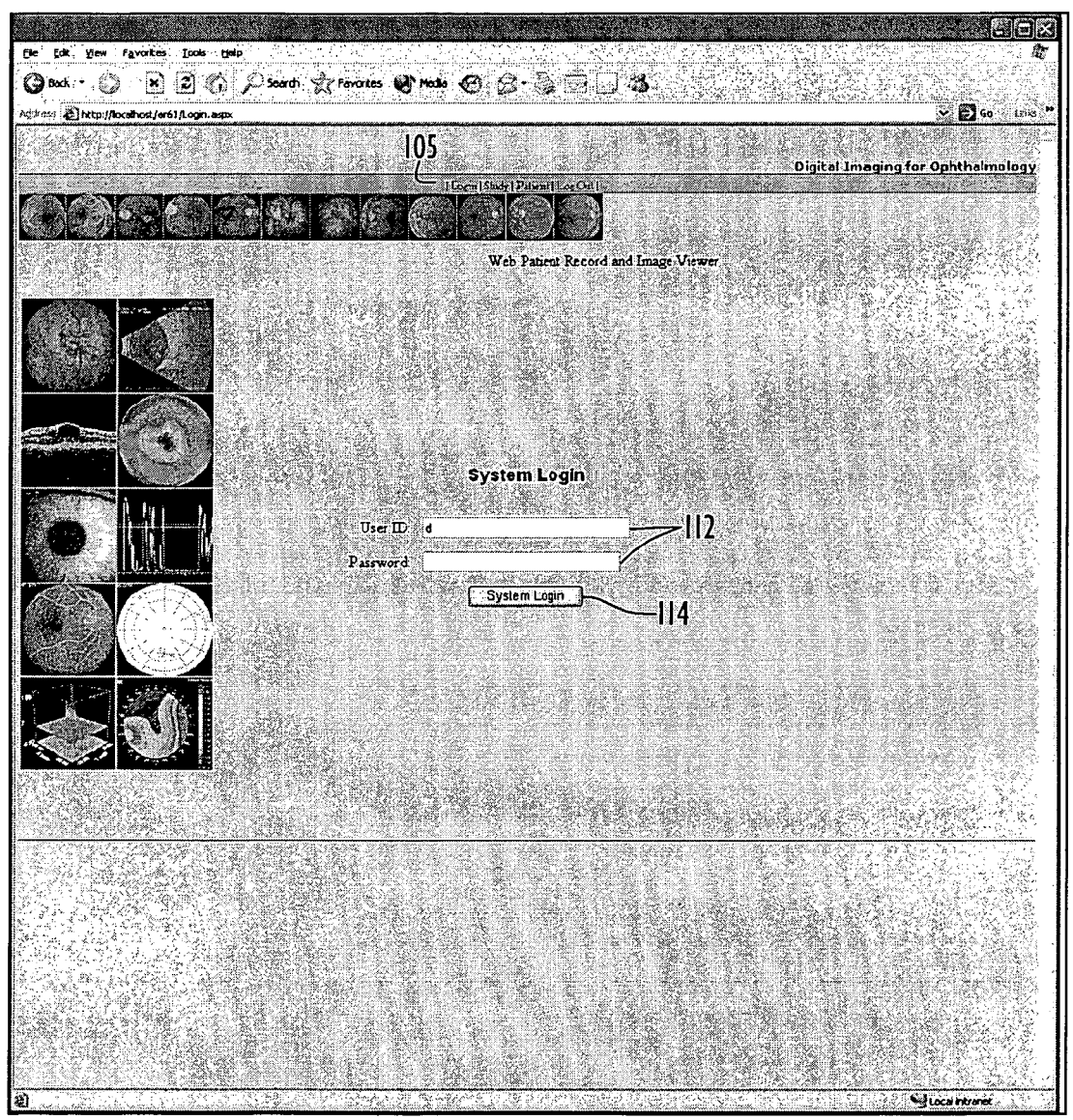
FIG. 6 is an illustration of an exemplary graphical user login screen employed by the present invention to authenticate users.
Figure 8:
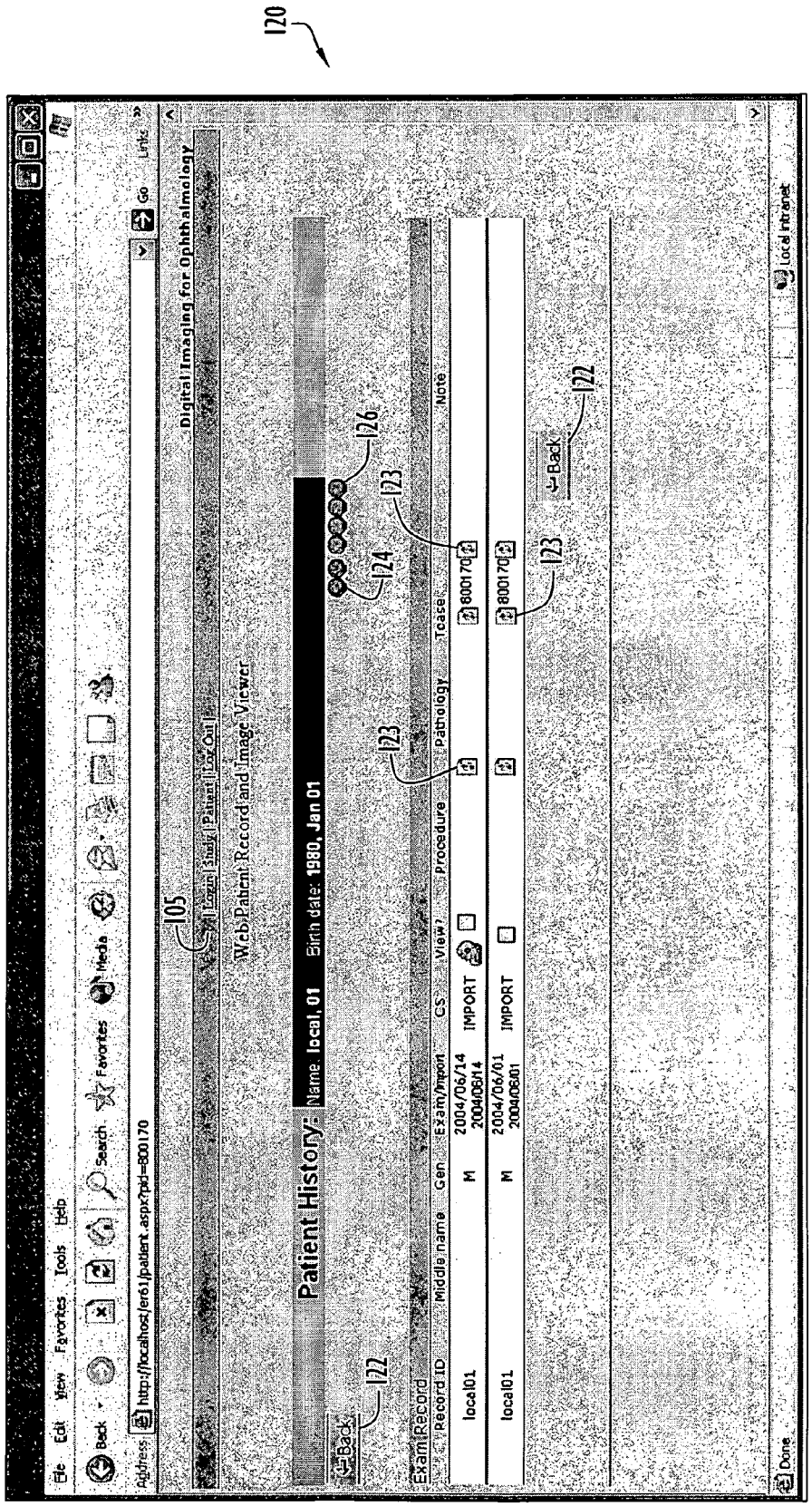
FIG. 8 is an illustration of an exemplary graphical user screen employed by the present invention to display patient history information.

Once the ophthalmologist has performed the analysis for patient examinations and images, the ophthalmologist subsequently diagnoses and/or treats the patient at step 78 (FIG. 5).

The system may further import files generated by capture stations, including those external or unconnected to image server 40 (FIG. 2) and stored in a memory or on a storage medium (e.g., viewing station, gateway or other device memory, CD ROM, DVD, floppy or other disk, etc.) as illustrated in FIGS. 15-20. Initially, a patient list screen or web page 200 (FIG. 15) is displayed in response to actuation of the Patient link within link menu 105 as described above. Patient list screen 200 is used to import examinations and to display imported examinations, and includes link menu 105 as described above and a list of the imported examinations.

Screen 200 is substantially similar to examination list screen 115 (FIG. 7) described above and shows imported patient examinations in the form of a table and listed by the importation date. Each table row provides information indicated by the table columns for a corresponding imported examination. By way of example only, the table columns include Select, Record ID, Center ID, Last Name, First Name, Gen, Birth Date, Imported, Modality, System ID, Pathology and Exam. The Select column includes an icon that enables selection of a patient for editing the patient record and mapping the patient to a physician. The system displays a patient edit screen or web page 220 (FIG. 17) in response to clicking on or actuating the icon. Screen 220 enables editing and mapping of the patient to a physician as described below.

The Record ID column indicates a Modality Patient ID generated by a specific capture station 12 or any other record generator. The Center ID column indicates the clinic center ID where the examination was performed. The Last and First name columns indicate the name of the patient, while the Gen column indicates the patient's gender. The Birth Date and Imported columns respectively indicate the birth date of the patient and date of importation. The Modality column indicates the modality type used for this examination (e.g., IMPORT, etc.).

The System ID column indicates a system generated identifier for a corresponding examination. The Pathology column indicates the diagnosis of a patient (e.g. Glaucoma, Choroidal Folds, Macular Pucker, etc.). This field can be modified under patient history screen 120 (FIG. 8) as described above. The Exam column includes an icon that enables display of an imported examination list screen or web page 230 (FIG. 18) to import new patient examinations as described below.

The table within screen 200 enables an ophthalmologist to search for specific studies. In particular, a search for imported examinations may be performed based on date or based on a category and corresponding value. With respect to a date search, screen 200 includes Today button 116, Last Seven Day button 118 and All button 119. These buttons are substantially similar to those described above for examination list screen 115 (FIG. 7). Today button 116 enables the system to retrieve all examinations with an importation date the same as the date of system use, while Last Seven Day button 118 retrieves all examinations imported within the last seven days. The All button enables retrieval of all imported examinations in the system.

A search may further be performed based on a category and corresponding value. Screen 200 includes drop-down list 111 containing the various categories and corresponding field 113 to receive a category value. By way of example only, the categories include: All Patients to display all examinations (e.g., values entered in the corresponding field are ignored); Patient Name (First and/or Last name) to search based on a patient's name using just first name, just last name or both first and last names (e.g., the name does not have to be completely spelled out, where the system searches for the patient's name that contains the field value); Doctor (First and/or Last name) to search based on the doctor's name using just first name, just last name or both first and last names (e.g., the name does not have to be completely spelled out, where the system searches for the doctor's name that contains the field value); Exam Procedure to search based on a procedure type for an examination (e.g. Color, Fluorescein, etc.), where the system searches for the procedure with the exact match; Pathology to search based on the diagnosis of a patient (e.g. Glaucoma, Choroidal Folds, Macular Pucker, etc.), where the system searches for pathology descriptions that contain the field value; Modality Patient ID (Record ID) to search based on a Modality Patient ID generated by a specific capture station or other record generator, where the system searches for the ID that contains the field value; System Patient ID to search based on the system generated system ID for the particular examination, where the system searches for the ID with the exact match; Modality (e.g., MRP, OCT3, TOPCON, IMPORT, etc.) to search based on the modality type used for the examination (e.g., IMPORT, etc.), where the system searches for the modality with the exact match; and Teaching Case Only to search based on the indication of a testing case (e.g., where values entered in the corresponding field are ignored). When a search category and value are entered, date search buttons 116, 118 or 119 are actuated to perform a search based on category and/or date.

Once the desired examination list is displayed, the list or table may be sorted by any item that includes a sort button icon 109 (e.g., Record ID, Center ID, Last Name, First Name, Gen, Birth Date, Imported, Modality, System ID and/or Pathology). The sort is alternately performed in descending/ascending order in response to successive icon actuations.

Screen 200 further includes page-setting features. By way of example only, these features include: a Total Records field that indicates the number of total records/examinations retrieved; a Records Per Page field that enables control of the quantity of records per page to be displayed (e.g., if this setting is changed, an icon needs to be actuated to apply the new setting); a Show Previous Page icon 101 to enable advancement to a previous page of the imported examination list; a Show Next Page icon 102 to enable advancement to the next page of the imported examination list; a Show First Page icon 103 to enable advancement to the first page of the imported examination list; and a Show Last Page icon 104 to enable advancement to the last page of the imported examination list. The screen may further include an X of Y indication to indicate the page number displayed relative to the number of pages available.

When a new patient examination is desired to be imported, new patient button 202 is actuated on patient list screen 200. This enables display of create patient screen or web page 210 (FIG. 16) including link menu 105 as described above and a plurality of fields and buttons. If a particular application designed for importation of files is being utilized, the file path and/or name of a desired file (e.g., XML file, etc.) on the viewing station or other storage unit may be entered in an appropriate Import Study File screen field. Alternatively, a browse button 212 may be used to locate the desired file. Once the file is located, an upload button 214 may be actuated to import the patient information.

If the file importation application is not utilized, patient information is entered in the corresponding screen fields. By way of example only, create patient screen 210 includes fields for customer ID (e.g., field is completed by system), import study file (e.g., described above for importation of a desired file), modality (e.g., in the form of a drop down list), clinic center ID, study (Record) ID1 and ID2, patient first, middle and last names, gender (e.g., in the form of a drop down list), patient date of birth, patient occupation, patient telephone number, patient e-mail address, patient home address (e.g., street address and zip code), comment, custom data, next visit date and pathology. The fields for customer ID, modality, study (Record) ID1, patient first and last names, patient gender and date of birth are typically required fields.

Once at least the required fields are completed, a create/import record button 216 is actuated to display patient edit screen 220 (FIG. 17) to check and/or edit patient information. This screen may also be displayed by actuating a Select column icon from patient list screen 200 (FIG. 15) as described above. Edit patient screen 220 includes link menu 105 as described above and a plurality of fields and buttons. By way of example only, edit patient screen 220 includes fields for customer, patient and modality IDs (e.g., fields are completed by system), clinic center ID, modality record ID1 and ID2, patient first, middle and last names, gender (e.g., in the form of a drop down list), patient date of birth, patient occupation, patient telephone number, patient e-mail address, patient home address (e.g., street address and zip code), comment, custom data, next visit date and physician. The fields for modality record ID1, patient first and last names, patient gender and date of birth are typically required fields.

Figure 15:
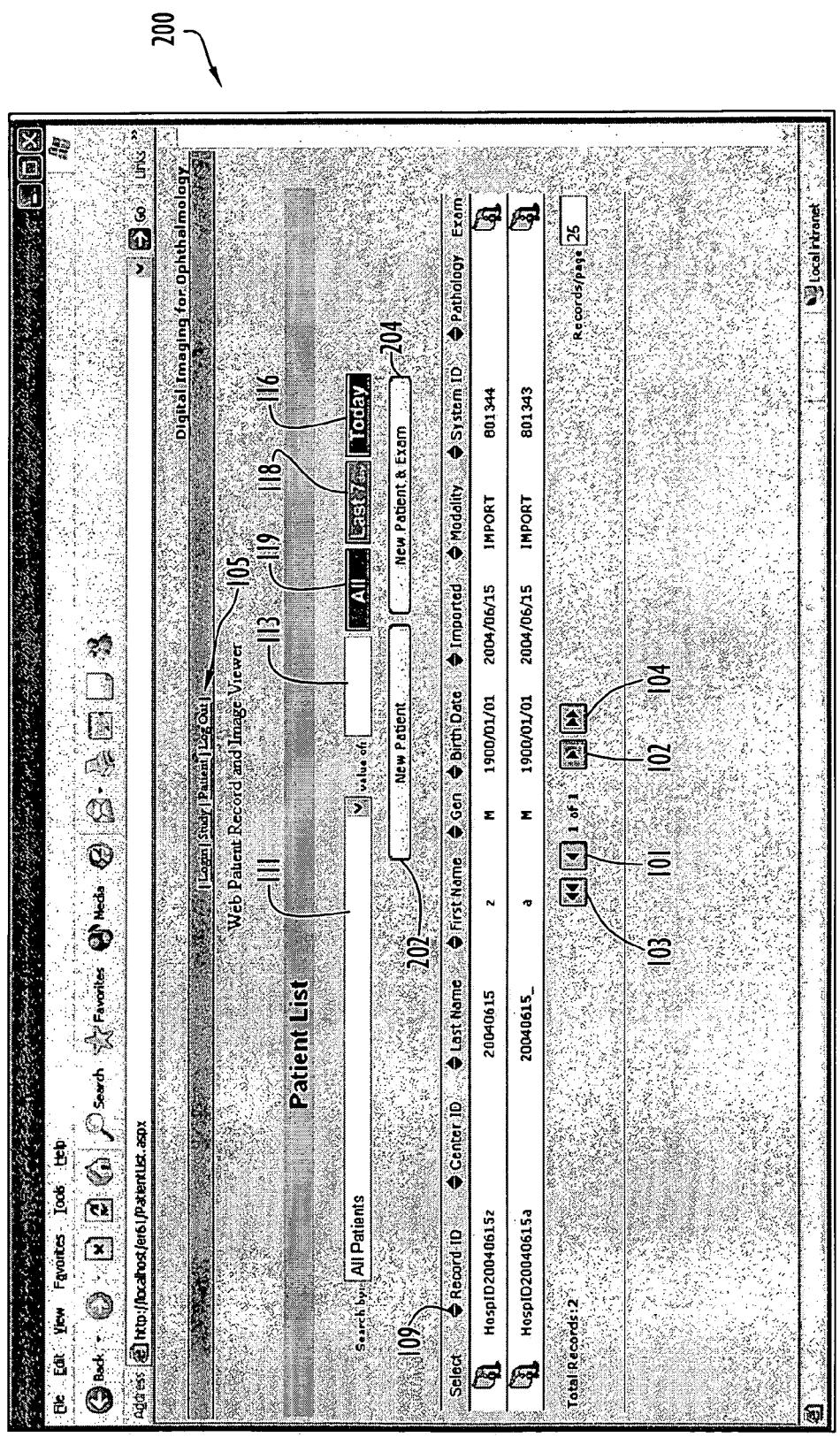
FIG. 15 is an illustration of an exemplary graphical user screen employed by the present invention for displaying imported examinations for patients.
Figure 16:
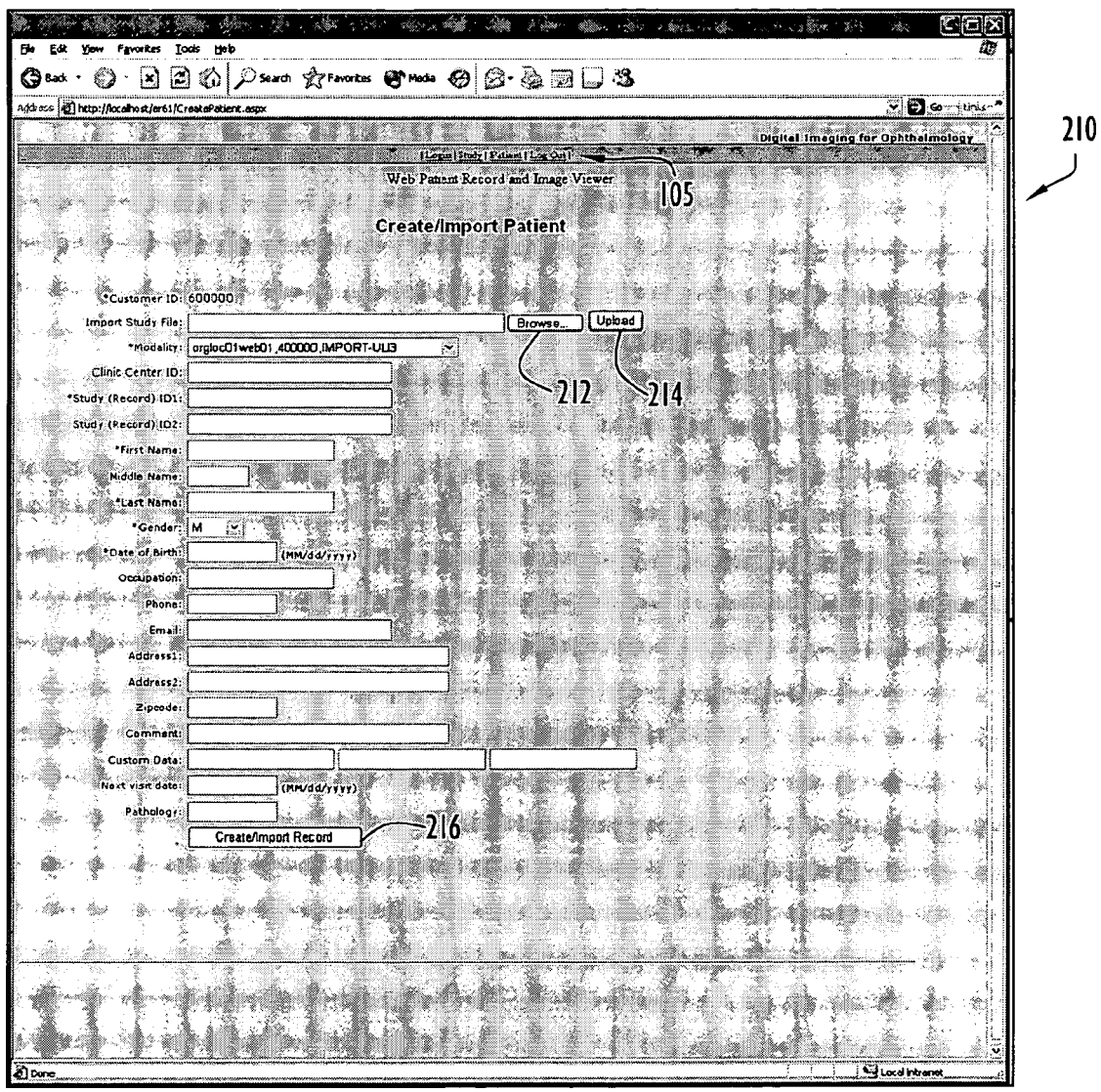
FIG. 16 is an illustration of an exemplary graphical user screen employed by the present invention for creating or importing a new patient record.
Figure 17:
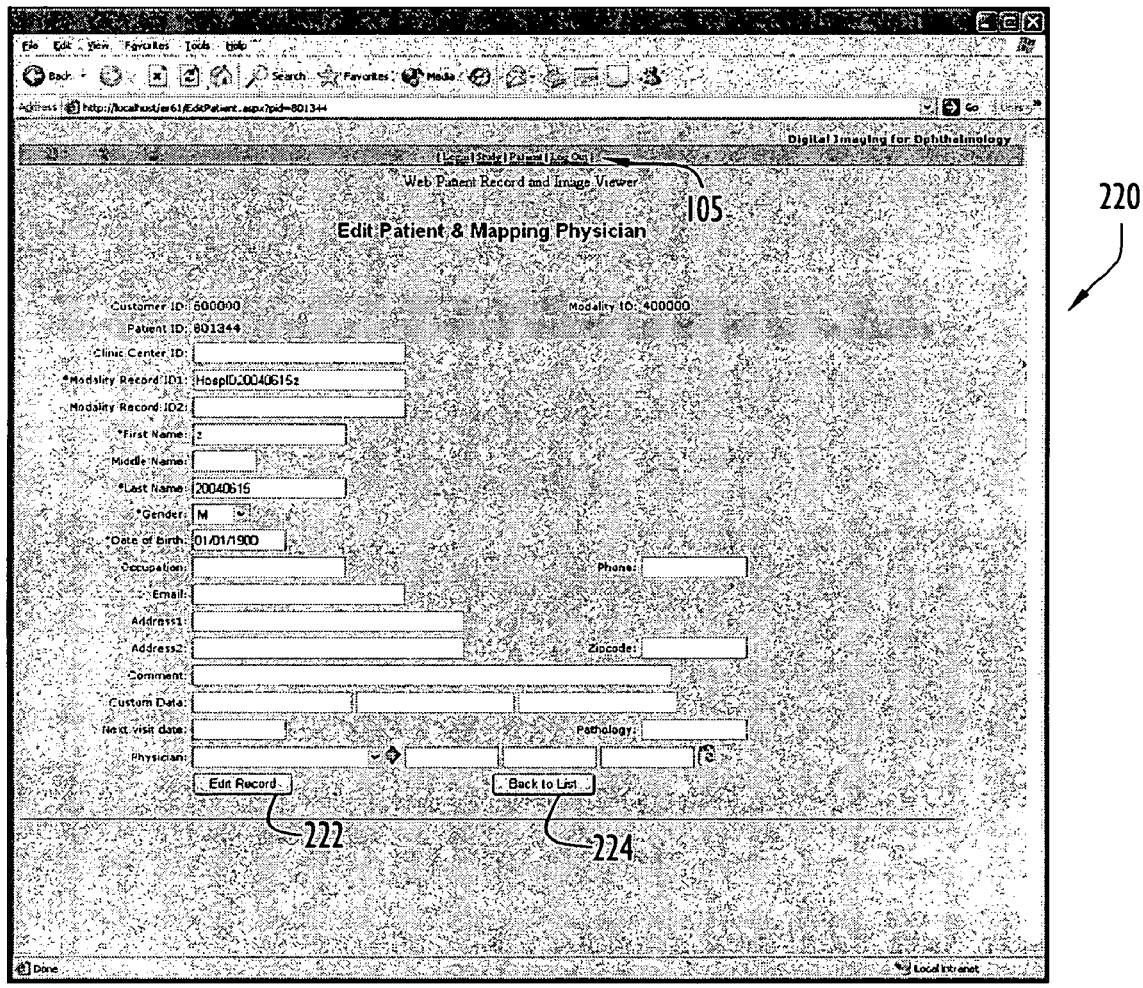
FIG. 17 is an illustration of an exemplary graphical user screen employed by the present invention for editing a patient record and associating a patient with a physician.

If the displayed patient information requires modification, the modifications are entered into the corresponding fields and an edit record button 222 is actuated to store the modifications and return to patient list screen 200 (FIG. 15). When the information has been verified and no modifications are performed, a back to list button 224 may be actuated to return to the patient list screen.

Figure 18:
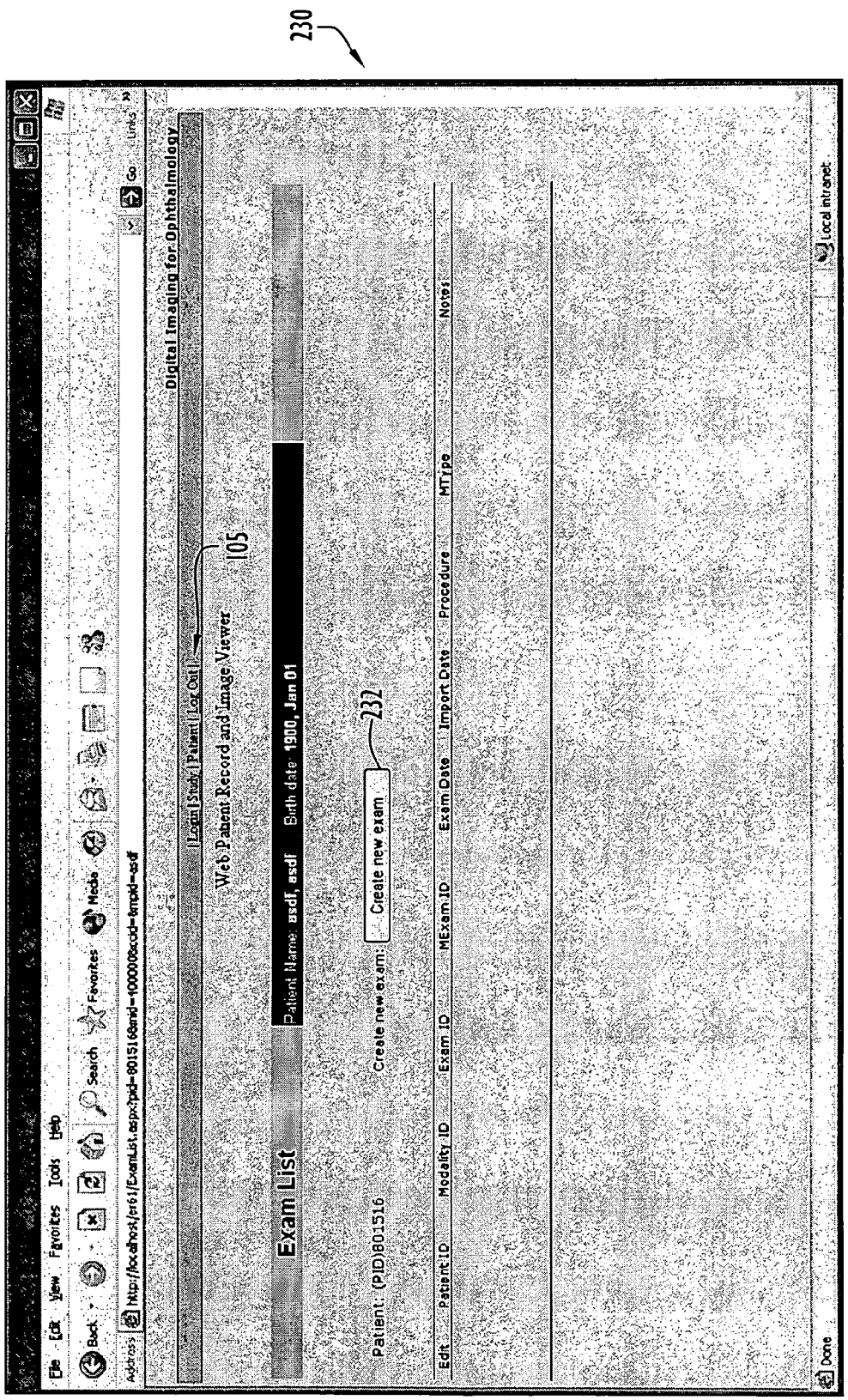
FIG. 18 is an illustration of an exemplary graphical user screen employed by the present invention for importing or re-importing an examination for a patient.
Figure 19:
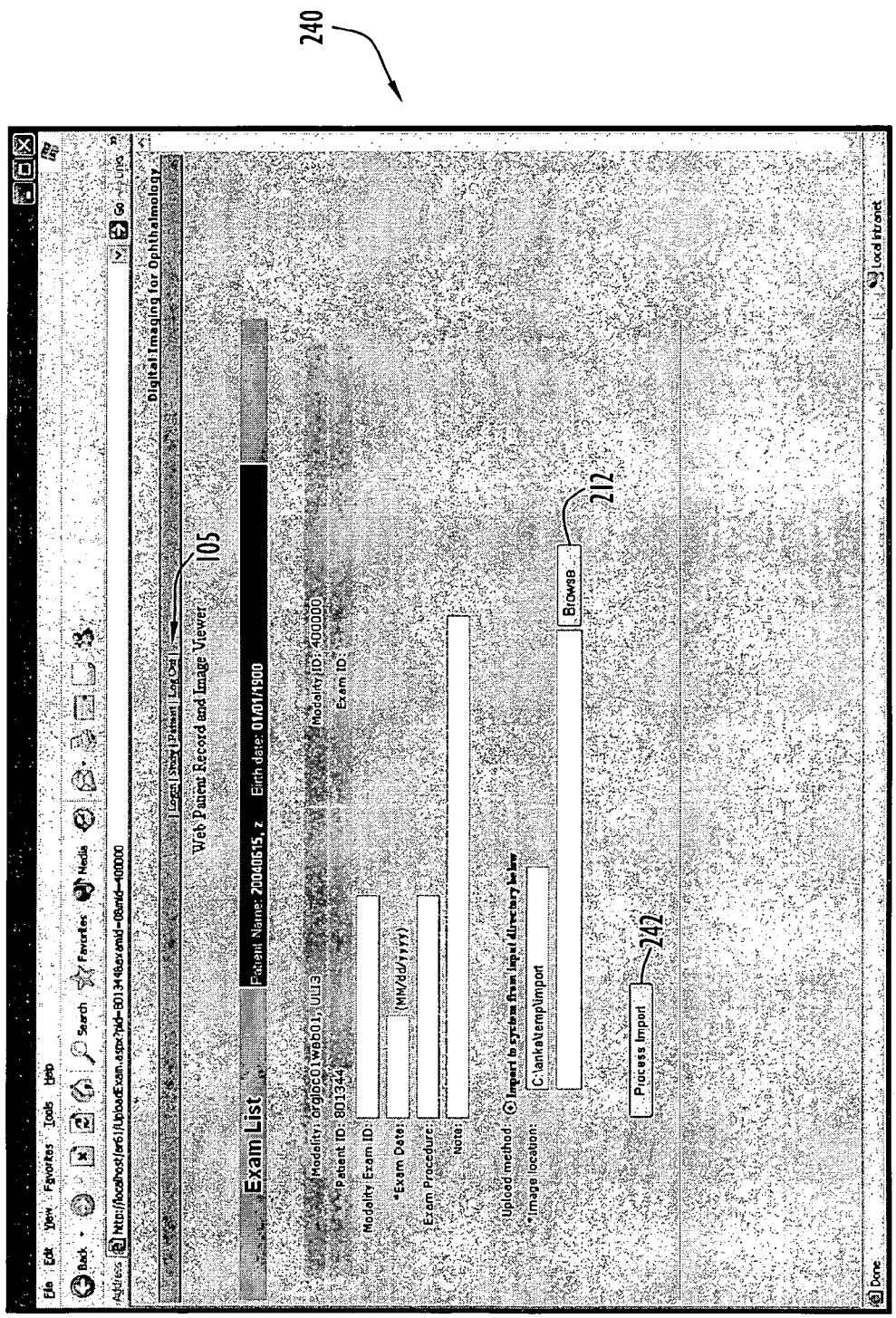
FIG. 19 is an illustration of an exemplary graphical user screen employed by the present invention for importing a new examination for a patient.
Figure 20:
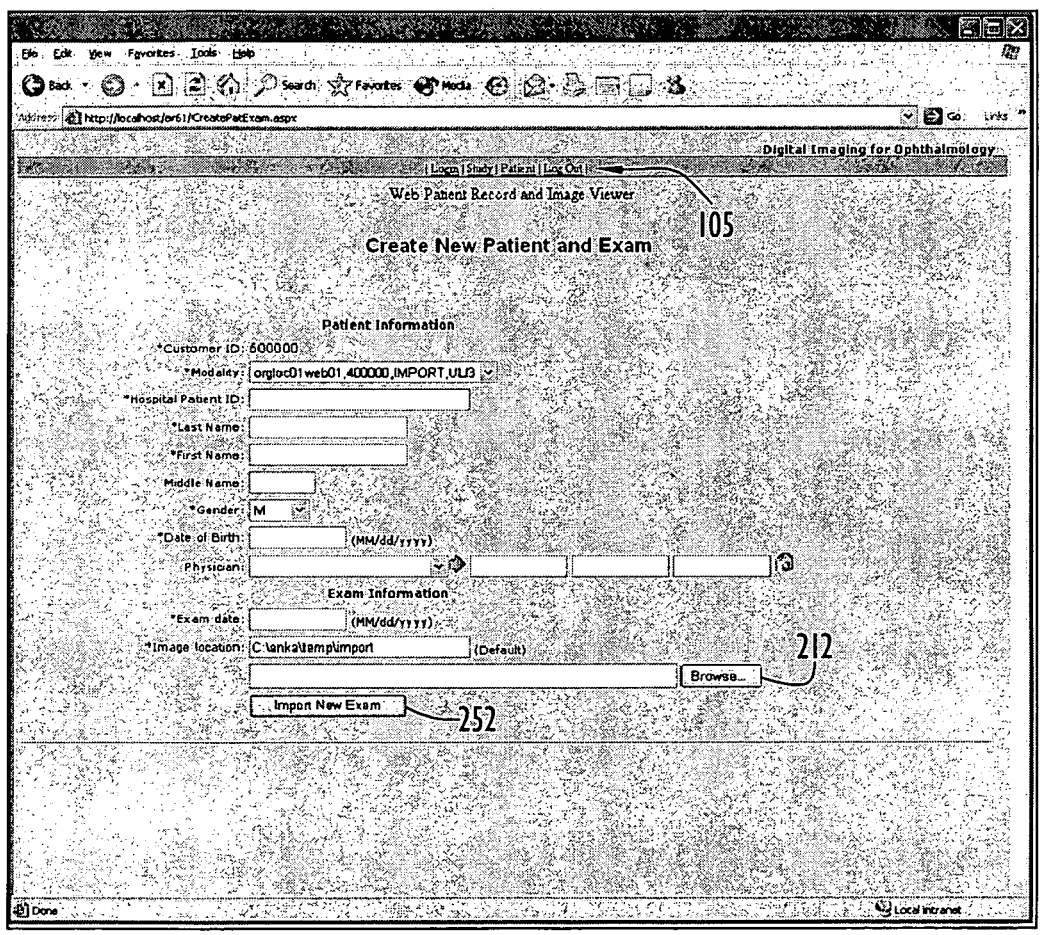
FIG. 20 is an illustration of an exemplary graphical user screen employed by the present invention for creating a new patient record and importing a new examination for that patient.
Figure 2I:
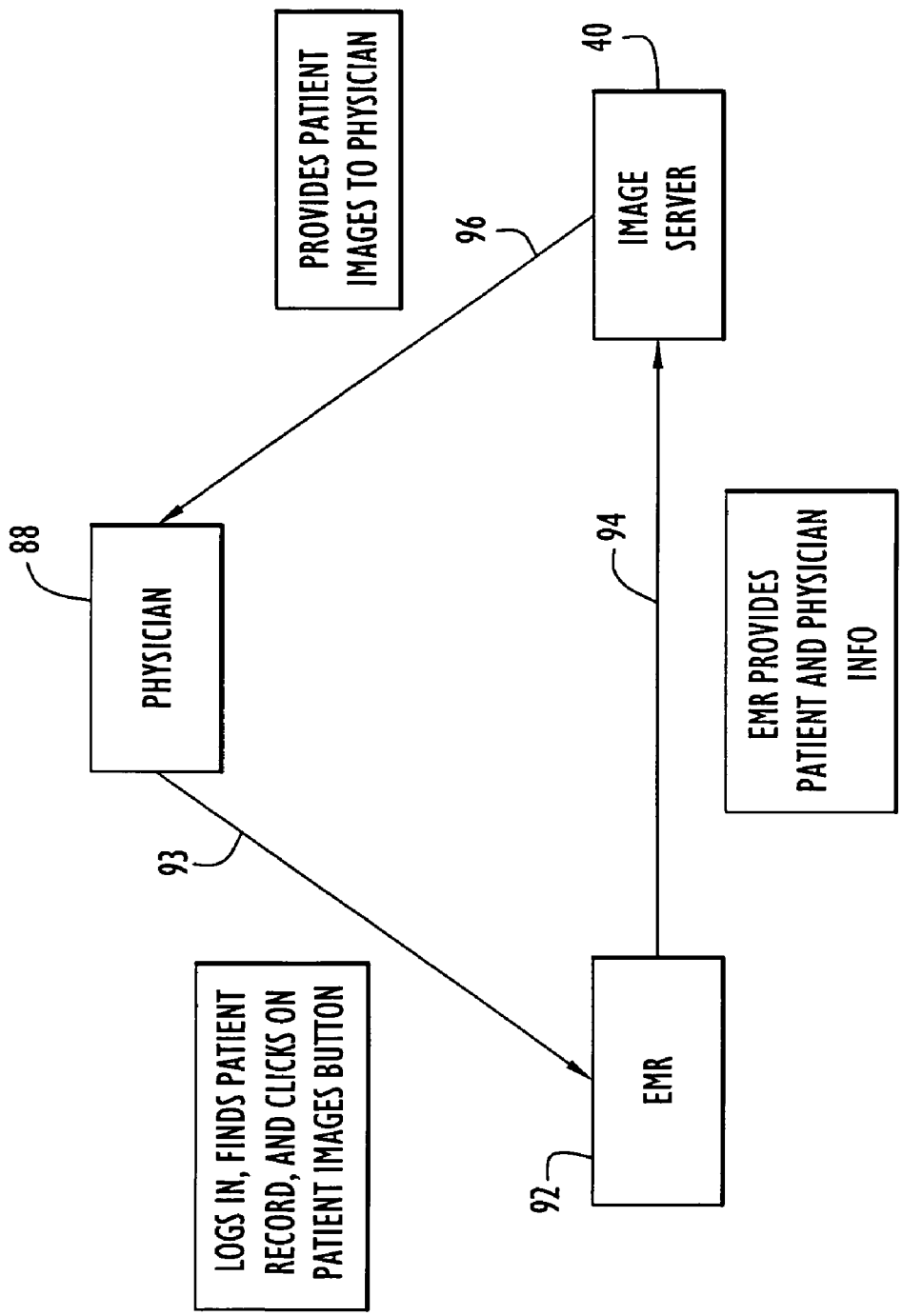

The ophthalmologist may actuate an exam column icon on patient list screen 200 (FIG. 15) and associated with a patient to display or import examinations for the selected patient. The actuation of the icon displays examination list screen 230 (FIG. 18). Screen 230 includes link menu 105 as described above and lists imported examinations for the selected patient. The patient Record ID, name and birth date are displayed at the top of the screen. Screen 230 shows imported patient examinations in the form of a table and listed by the examination date. Each table row provides information indicated by the table columns for a corresponding imported examination. By way of example only, the table columns include Edit, Patient ID, Modality ID, Exam ID, MExam ID, Exam Date, Import Date, Procedure, MType and Notes.

The Edit column includes icons that enable selection of an examination for importation or re-importation of the study and corresponding images. Actuation of the icon displays a create new exam screen or web page 240 (FIG. 19) to perform the importation as described below. The Patient ID column indicates a patient identification, while the Modality ID column indicates a modality ID generated to reference the modality used to create the study. The Exam ID column indicates a system generated reference number for the examination. The MExam ID column indicates a modality generated reference number for the examination, if any. The Exam Date column indicates an actual examination date of the study. The Import Date column indicates when the examination is imported into the system. The Procedure column indicates the procedure type for the examination (e.g. Color, Fluorescein, etc.), while the MType column indicates a modality description. The Notes column includes notes for the examination.

In order to import a new examination for the patient, a create new exam button 232 is actuated on screen 230. Actuation of this button displays create new examination screen 240 (FIG. 19) to import new examinations for the patient. This screen may also be displayed to re-import examinations for patients selected via actuation of Edit column icons on screen 230 as described above. Screen 240 includes link menu 105 as described above and a plurality of fields and buttons. The patient name and birth date are displayed at the top of the screen, while patient information is entered in the corresponding screen fields. By way of example only, create new examination screen 240 includes fields for modality (e.g., field is completed by system), modality ID (e.g., field is completed by system), patient ID (e.g., field is completed by system), examination ID (e.g., field is completed by system), modality examination ID, examination date, examination procedure, note and image location. The fields for examination date and image location are typically required fields.

A file path and/or name of a desired image file on the viewing station or other storage unit may be entered in the image location screen field. Alternatively, a browse button 212 may be used to locate and enter the desired file in the image location field. Once at least the required fields are completed, a process import button 242 is actuated to import the examination for the patient.

A new patient examination may alternatively be imported by actuating new patient and exam button 204 on patient list screen 200 (FIG. 15). This enables display of a create new patient and examination screen or web page 250 (FIG. 20) including link menu 105 as described above and a plurality of fields and buttons. By way of example only, screen 250 includes fields for customer ID (e.g., field is completed by system), modality (e.g., in the form of a drop down list), hospital patient ID, patient first, middle and last names, gender (e.g., in the form of a drop down list), patient date of birth, physician, examination date and image location. The fields for customer ID, modality, hospital patient ID, patient first and last names, patient gender, date of birth, examination date and image location are typically required fields.

A file path and/or name of a desired image file on the viewing station or other storage unit may be entered in the image location screen field. Alternatively, a browse button 212 may be used to locate and enter the desired file in the image location field. Once at least the required fields are completed, an import new exam button 252 is actuated to import the examination for the newly entered patient.

The system of the present invention may be interfaced with an electronic medical record (EMR) system that contains various patient information and is typically utilized by physicians to manage patient information. The electronic medical record system is typically implemented by a computer system (e.g., base, monitor, keyboard or other input device, etc.) with appropriate hardware and/or software modules to perform the patient information management and communication functions described below. The present invention image server functions as a seamlessly integrated subsystem of an overall coordinating electronic medical record (EMR) system. A manner of integrating the image server with an electronic medical record system is illustrated in FIG. 21. This type of interface is utilized for the case where the electronic medical record (EMR) system is capable of calling an external web address (e.g., URL, etc.) with patient specific parameters. In response to this call from the electronic medical record (EMR) system, the image server directly displays patient specific data in a browser window of a physician end-user system as described below.

Initially, image server 40 is substantially similar to the image server described above and is coupled to an electronic medical record (EMR) system 92 of a physician or ophthalmologist 88 via a network (e.g., Internet; not shown). Physician 88 logs into the electronic medical record system and locates desired patient examination records at flow 93. The electronic medical record (EMR) system provides a customized images button for each patient that is displayed with patient information. When the physician actuates (e.g., clicks on) this button, the electronic medical record (EMR) system sends the desired patient and physician information to image server 40 at flow 94. This is typically accomplished by the physician actuating the images button within the patient information displayed by the electronic medical record (EMR) system. The actuation of the images button directs the electronic medical record system (EMR) to call the web address of the image server with the desired information as described above.

In response to the call from the electronic medical record (EMR) system, the image server (e.g., web viewing application 45) logs the physician into the system (e.g., based on the information within the call) and verifies that the physician is allowed to view the images for the identified patient as described above. Once the physician is verified, the image server retrieves the appropriate information and provides the physician with the appropriate web pages or screens at flow 96. In particular, the image server produces patient history screen 120 (FIG. 8) described above with the desired patient information. If the image server does not contain information for the desired patient (e.g., typographical error by the physician, no images for the patient, etc.), the image server provides the patient history screen without any examinations. The physician may manipulate the patient history screen to view desired images and/or navigate to other screens in substantially the same manner described above. The physician may further mark desired images and store the marked images (e.g., via a drag and drop operation) in the electronic medical record (EMR) system. After the physician has examined the images and performed desired operations, the image server session may be terminated.

Figure 22:
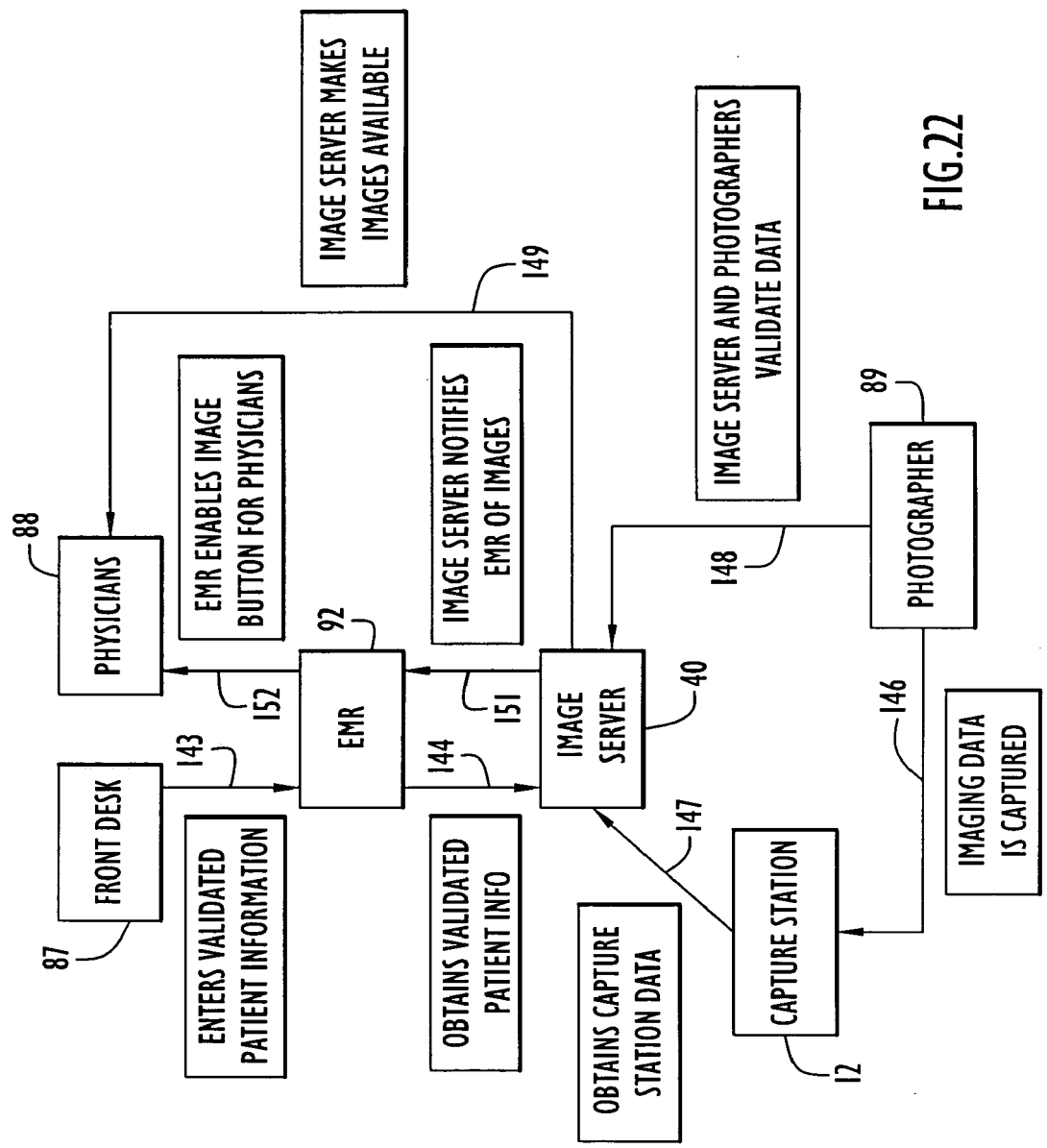
FIG. 22 is a system flow diagram of the image server integrated with an electronic medical record system and providing data validation according to the present invention.

An alternative manner of integrating the image server with an electronic medical record (EMR) system is illustrated in FIG. 22. In this case, patient information from the electronic medical record system is validated by the image server prior to importation of patient examinations from the capture station. The validation detects data entry errors, thereby reducing searches by the physician for misplaced examinations.

Initially, image server 40 is substantially similar to the image server described above and is coupled to electronic medical record (EMR) system 92 of a physician or ophthalmologist 88 via a network (e.g., Internet; not shown). The electronic medical record (EMR) system is substantially similar to the electronic medical record system described above. Capture station 12 is substantially similar to the capture station described above and is coupled to image server 40 via internal and/or external gateway units (FIGS. 2 and 4A-4B) and the network as described above.

Patient information is entered into electronic medical record (EMR) system via front desk or physician office personnel 87 at flow 143. Image server 40 receives patient information from the electronic medical record (EMR) system at flow 144. The electronic medical record system may send the patient information (e.g., at predetermined intervals, based on certain conditions, as the information is entered, etc.) or the image server may poll the electronic medical system for the information. The information may be transferred via a conventional networking interface or protocol (e.g., HL7, web-services, SQL queries, etc.). Photographers 89 generate corresponding patient images at flow 146 via capture station 12.

The image server receives the examination images from the capture station at flow 147 in substantially the same manner described above. The photographers subsequently enter the patient information via the web pages or screens to import into or store the examinations in the image server as described above. The entered information is compared with the information received from the electronic medical record (EMR) system at flow 148. If image information matches corresponding patient information received from the electronic medical record system, the image server stores the examination images. When image information does not match the corresponding patient information, a web page or screen is displayed with the invalid examination information to enable the photographer to edit or otherwise resolve the problematic information. In other words, the image server only stores examination images with information corresponding to the information received from the electronic medical record (EMR) system.

Once validated information is stored, the image server makes the validated information available for viewing by physicians 88 at flow 149 (e.g., the physicians may access the image server directly over a public network to view the images as described above). The image server further notifies the electronic medical record system (EMR) of the availability of those images via a networking interface or protocol (e.g., HL7, web-services, web pages, SQL queries, etc.) at flow 151. In response to the notification, the electronic medical record (EMR) system provides an image button in the patient record at flow 152 to enable physicians 88 to access the images through the electronic medical record (EMR) system in substantially the same manner described above for FIG. 21.

It will be appreciated that the embodiments described above and illustrated in the drawings represent only a few of the many ways of implementing a system and method for efficient diagnostic analysis of ophthalmic examinations.

The computer systems (e.g., viewing station, modality, image server, redundant server, etc.) may be implemented by any personal or other type of computer system (e.g., IBM-compatible, Apple, Macintosh, laptop, palm pilot, etc.). The computer systems may include any commercially available operating system (e.g., Windows, OS/2, Unix, Linux, etc.). The computer systems may further include any commercially available or custom software (e.g., server software, browser software, viewing software, etc.), database and/or database management systems. The computer systems may further include any types of input devices (e.g., keyboard, mouse, voice recognition, etc.) to navigate the screen, enter information and/or actuate buttons or icons. The databases may be implemented by any conventional or other database or storage structure (e.g., file, data structure, etc.). The redundant server may be of any quantity and may lag or transfer information from the image server at any desired time intervals (e.g., seconds, minutes, hours, days, etc.).

It is to be understood that the software for the computer systems (e.g., viewing station, modality, image server, redundant server, etc.) and/or gateway units may be implemented in any desired computer language and could be developed by one of ordinary skill in the computer arts based on the functional descriptions contained in the specification and flow charts illustrated in the drawings. By way of example only, the software of the present invention (e.g., image server, viewing station, etc.) may be developed utilizing JAVA Script, HTML, Visual Basic Script, MS C#, .NET Technology and/or C++ computer languages. The computer systems may alternatively be implemented by any type of hardware and/or other processing circuitry. The various functions of the computer systems and gateway units may be distributed in any manner among any quantity of software modules, processing or computer systems and/or circuitry. The software and/or algorithms described above and illustrated in the flow charts may be modified in any manner that accomplishes the functions described herein.

The networks (e.g., public, private, virtual private, etc.) may be implemented by any communications network (e.g., LAN, WAN, Internet, Intranet, VPN, etc.). The computer systems and/or gateway units may include any conventional or other communications devices to communicate over the networks via any conventional or other protocols. The functions of the image server may be distributed among the image server, redundant server, viewing station, gateway units and/or modality in any desired fashion.

The storage system database may be implemented by any quantity of any conventional or other database or storage unit. The database may store any desired information. The file system may be implemented by any quantity of any conventional or other file storage system and may store any desired information. The codes and images may be stored within the file system and/or database in any desired fashion (e.g., the file system and database may individually or collectively store the codes and images in any desired combination or fashion, etc.). The image server may utilize any desired codes to validate images (e.g., checksum, hash code, assign unique identifiers, etc.). The system may be utilized with or without the image validation.

The archive system may be implemented by any quantity of any conventional or other storage system. The archive system may store any desired information or perform any type of back-up (e.g., store original images, compressed images, codes, etc.). The monitor module may monitor, detect and/or measure any desired system conditions or parameters and provide reports containing any desired information in any suitable arrangement. The reports may be sent to any desired location via any conventional or other communication techniques (e.g., electronic mail or other electronic message, etc.). The order module may enable ordering of any desired examination or procedure, where orders may be sent to any desired location via any conventional or other communication techniques (e.g., electronic mail or other electronic message, etc.)

The image server and/or gateway units may communicate and/or retrieve information from any quantity of modalities utilizing any desired formats or interfaces. The images within the modalities may be associated with any patients and/or examinations via any suitable identifiers (e.g., alphanumeric, symbols, etc.). The image server and/or gateway units may poll the modalities at any desired intervals to retrieve information. The information may be retrieved based on any suitable criteria (e.g., examination of timestamps or other identifiers indicating new images, etc.). The button or switch may be implemented in any fashion (e.g., software, hardware signal, etc.) to enable the image server or gateway unit to access the modality.

The gateway units may send the large original image file to the image server upon receipt of that image. Alternatively, the original image file may be sent to the image server at any desired time (e.g., preferably at times of low network utilization, at night, etc.). The gateway units may employ any conventional or other techniques to produce any desired type of images (e.g., compressed, thumbnail, etc.). The gateway units may provide the images in any desired formats (e.g., JPEG, PDF, TIFF, etc.). The compressed and/or original image files may be sent to the image server individually or in any combination (e.g., only the original image file may be transferred, only the compressed image file may be transferred, both types of image files may be transferred, etc.).

The image server may utilize any conventional or other caching techniques (e.g., transmit images in any order, utilize any techniques (e.g., FIFO, etc.), proactively transfer images to locations based on any suitable criteria (e.g., location of user associated with image, etc.), etc.) to transmit data to locations local to the viewing stations (e.g., to the viewing stations, to local gateway units, etc.) prior to requests for that data. The cache memories (e.g., gateway unit, viewing station, etc.) may be implemented by any conventional or other storage device and may include any desired storage capacity. The cache memories may store any desired quantity of images (e.g., compressed, thumbnail, original) or store images received during any desired time interval (e.g., days, etc.). The compressed and/or original image files may be sent to the viewing stations (e.g., from the images server and/or gateway units) individually or in any combination (e.g., only the original image file may be transferred, only the compressed image file may be transferred, both types of image files may be transferred, etc.). The cache scheduler module may send the images to the local locations (e.g., cache memories of the gateway units and/or viewing stations) at any desired time intervals or in response to any suitable conditions (e.g., receipt of new images, etc.). The image server may associate users with locations in any desired fashion (e.g., zones, areas, etc.) and based on any suitable identifiers (e.g., IP or other addresses of any local components (e.g., viewing station, gateway unit, etc.), etc.).

The various topologies (e.g., FIGS. 4A-4B) for enhanced transfer of images may be arranged in any desired fashion and include any quantity of components (e.g., gateway units, viewing stations, image server, etc.). The remote sites may include any quantity of components (e.g., gateway units, viewing stations, image server, etc.) arranged or in communication with each other in any desired fashion.

The display screens or web pages and windows may be arranged in any fashion and contain any type of information (e.g., images of any desired human or animal anatomy (e.g., eye, etc.), images of any tests, etc.). The display screens or web pages and windows may be navigated or viewed in any desired order or fashion. The screens may include any quantity of any type of buttons or icons of any shapes, sizes or colors and disposed at any locations to initiate any desired actions or indicate any desired conditions. The screens may include any quantity of any type of fields (e.g., fill in, drop down menus or lists, etc.) of any shapes or sizes disposed at any locations to receive information from the system and/or user and/or to display information. The system may automatically log out a user after any desired time interval and may track any desired information pertaining to a session (e.g., examinations and/or images accessed by a particular user, the time and/or duration of the session, the viewing station utilized, etc.). The system may display and/or receive information via any input mechanisms (e.g., screens, menus, line prompts, forms, fields, etc.) or input devices (e.g., keyboard, mouse, voice recognition, etc.). The brightness, contrast and other settings may utilize any type of control (e.g., bars, buttons, etc.) and indicate the settings relative to any scale (e.g., percent, intensity, etc.). The measurements may be determined in any desired units (e.g., feet, inches, centimeters, millimeters, meters, etc.). The system may limit user access to information in any desired fashion and based on any suitable criteria (e.g., users may be limited to viewing information of associated patients, of testing cases, etc.).

The tables may be arranged in any fashion and include any information listed in any desired order (e.g., based on any information). The search may be performed based on any desired searching criteria (e.g., any table or database field, dates or range of dates, etc.). The table entries may be sorted in any desired fashion or order based on any quantity of any desired table columns. The system may display in any fashion any quantity of images or patient information for comparison or other purposes. The system may store any quantity of any desired annotation or other files associated with an image for any quantity of users. The system may enable review and/or verification by any quantity of any desired users based on an any conditions or criteria (e.g., updated or new images, status of a user, etc.).

The image server and/or redundant server may be utilized in combination with any suitable medical information system (e.g., electronic medical record (EMR), etc.) in any desired fashion to provide images and/or transfer patient and/or other information. The medical information system may provide any suitable icon or other indicator to indicate the capability of retrieving images. The images displayed by the system may be stored to the medical information system or a viewing system via any conventional or other techniques (e.g., commands, drag and drop, etc.). The medical information system may utilize any conventional or other techniques to access the image server (e.g., networking protocols, invoke a web call, etc.) and may provide any suitable information or parameters. The image server may validate patient information between the images and medical information in any desired fashion (e.g., comparison, etc.) and may display any suitable screen, web page or message indicating images with invalid or inconsistent information.

The viewing station or remote location may include any type of wireless or other sensing device to detect medical personnel. The medical personnel may include any type of wireless or other device to enable detection at the remote location or viewing station and to provide information to the viewing station. The information may enable any desired system action (e.g., automatic login, searching, caching or transmission of associated images to locations local to the user, etc.). Further, the wireless card may be in the form of a remote processing device (e.g., PDA, etc.) to enable remote access to the viewing station.

The present invention may employ various techniques to validate examination images for display. For example, a measurement or dimension validation may be performed on the images. The maximum dimensions (e.g., length, width, etc.) for the images may be stored and compared to dimensions of an image for display determined by the system. The comparison may be performed with respect to any desired units (e.g., inches, centimeters, etc.). An error message may be displayed to notify the user of an image with invalid dimensions.

It is to be understood that the terms "top", "bottom", "side", "upper", "lower", "front", "rear", "horizontal", "vertical" and the like are used herein merely to describe points of reference and do not limit the present invention to any specific configuration or orientation.

The present invention is not limited to the applications disclosed herein, but may be utilized for any type of medical or other application to enable remote viewing of images and other information to perform analysis.

From the foregoing description, it will be appreciated that the invention makes available a novel system and method for efficient diagnostic analysis of ophthalmic examinations, wherein a digital medical diagnostic system enables ophthalmologists to view patient and other images remotely to diagnose various conditions.

Having described preferred embodiments of a new and improved system and method for efficient diagnostic analysis of ophthalmic examinations, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system enabling remote access of medical images generated by image capture stations over a network comprising:
    a processing system configured to retrieve at least one medical image from among a plurality of remote image capture stations generating said medical images for transmission over said network to at least one remote viewing station, said processing system including:
        a station interface unit configured to automatically retrieve said generated medical images from said image capture stations in response to conditions indicating generation of new medical images, wherein at least two image capture stations include different station interfaces configured for retrieving said generated medical images therefrom, and said station interface unit includes a plurality of station interfaces configured to interface different ones of said remote image capture stations to retrieve said medical images;
        a storage system configured to store said retrieved medical images from said image capture stations and associated information;
        a user interface module configured to generate a user interface for display and manipulation of said retrieved medical images, and to receive and process requests from said at least one remote viewing station for said retrieved medical images and enable transference of said requested medical images to said at least one remote viewing station; and
        a communication module configured to facilitate communications over said network to enable said medical image retrieval and remote access to said retrieved medical images.

2. The system of claim 1, wherein said medical images include ophthalmic images.

3. The system of claim 1, wherein said processing system further includes:
    a code generation module configured to generate a specific code for each medical image based on data within that image;
    wherein said storage system includes:
        a database configured to store said code associated with each medical image; and
        a file system configured to store said retrieved medical images.

4. The system of claim 3, wherein said processing system further includes:
a change detection module configured to detect changes in medical images subsequent storage in said file system based on a change in said associated code.

5. The system of claim 3, wherein each viewing station includes:
a viewing interface module configured to display said user interface from said processing system including retrieved medical images; and
a validation module configured to regenerate a code for said retrieved medical image of said user interface and compare said regenerated code to said code for that image stored in said database, wherein said viewing interface module is configured to display retrieved medical images in response to validation by said validation module.

6. The system of claim 5, wherein said network includes the Internet and said viewing interface module includes a browser.

7. The system of claim 6, wherein said browser includes image manipulation controls to enable a user to manipulate medical images displayed on a viewing station.

8. The system of claim 6, wherein said browser includes image measurement controls to enable a user to measure areas within said medical images displayed on a viewing station.

9. The system of claim 8, wherein said user interface module includes:
a measurement selection module configured to enable a user to select image resolution prior to performing measurement of said areas.

10. The system of claim 6, wherein said user interface module includes:
a settings module configured to maintain display settings during display of said medical images by said user on a viewing station.

11. The system of claim 3, wherein said file system is configured to store said retrieved medical images and compressed versions of those medical images, and said processing system further includes:
an archive system configured to selectively perform storage back-up operations for said information within said storage system, wherein said back-up operations include storing at least one of: said codes within said database; said codes and said compressed versions of said medical images; and said codes, said medical images and said compressed versions of said medical images.

12. The system of claim 1 further including:
a redundant processing system configured to assume functions of said processing system in response to a failure of said processing system, wherein said redundant processing system is configured to store information from said processing system and lags said processing system with respect to said stored information by a predetermined interval.

13. The system of claim 1, wherein said processing system further includes:
a monitor module configured to detect various conditions of said system and report said conditions to a remote system operations center without requiring a private network connection to the remote operations center.

14. The system of claim 1, wherein said user interface module further includes:
a security module configured to control access to said medical images, wherein said security module includes:
a track module configured to store information pertaining to user sessions including at least one of users accessing said system, time of access and patients accessed by said user;
a termination module configured to terminate a user session in response to predetermined conditions; and
an access module configured to control information accessed by said user, wherein said access is at least one of unlimited, limited to medical examination information associated with said user and limited to test case information without demographic data.

15. The system of claim 1, wherein said user interface module includes:
a comparison module configured to generate a user interface for displaying a plurality of medical images for comparison of those images by a user.

16. The system of claim 1, wherein said user interface module includes:
a verification module configured to enable a user to verify a medical image retrieved from said image capture stations and to indicate a verification status of said retrieved medical images.

17. The system of claim 16, wherein said verification module includes:
an update module configured to indicate a status of a medical image as unverified in response to modifications to that image.

18. The system of claim 1, wherein said user interface module includes:
a review module configured to enable a user in the form of a medical practitioner to review a medical image retrieved from said image capture stations and to indicate a review status of said retrieved medical images.

19. The system of claim 18, wherein said review module includes:
an update module configured to indicate that a medical image lacks review in response to modifications to that image.

20. The system of claim 1, wherein said processing system further includes:
a cache module configured to transfer medical images from said storage system to locations local to said at least one viewing station prior to requests for those images from said at least one viewing station.

21. The system of claim 20 further including a plurality of gateway units each disposed at a different site remote from said processing system, wherein each gateway unit is coupled to said processing system and a corresponding image capture station and includes:
a retrieval module configured to receive medical images from a corresponding image capture station;
a compression module configured to generate compressed versions of said retrieved medical images;
a cache memory configured to store said retrieved medical images and said compressed images; and
a transfer module configured to transfer said stored images to said processing system.

22. The system of claim 21, wherein said transfer module includes:
a scheduling module configured to transfer said compressed images to said processing system prior to transference of said uncompressed medical images.

23. The system of claim 22, wherein said scheduling module is configured to transfer uncompressed medical images at times of low utilization of said network.

24. The system of claim 21, wherein at least one viewing station includes a cache memory and said cache module is configured to transfer medical images from said storage system to at least one of said viewing station cache memory and said gateway unit cache memory.

25. The system of claim 24, wherein said user interface module further includes:
  a location module configured to determine a location of a user accessing said system; and
  an image module configured to direct retrieval of a requested image from an image location in accordance with said user location and a storage location of said requested image,
wherein said image location includes one of a cache memory of a viewing station of said user, a cache memory of a gateway unit local to said user and said storage system.

26. The system of claim 1 further including:
  a medical information system configured to maintain information associated with patients, wherein said medical information system is coupled to said processing system via said network to access said medical images.

27. The system of claim 26, wherein said network includes the Internet and said medical information system is configured to access said processing system via a call to an Internet address of said processing system, and wherein said call includes parameters to access desired information.

28. The system of claim 26, wherein said medical information system is configured to access said processing system via networking protocols to transfer information with said processing system, and said processing system includes:
  a verification module configured to verify patient information received from said medical information system with information associated with said medical images and to identify medical images associated with information inconsistent with said information from said medical information system.

29. A method of enabling remote access over a network of medical images generated by remote image capture stations and stored in a processing system comprising:
  (a) automatically retrieving said generated medical images from said image capture stations in response to conditions indicating generation of new medical images, wherein at least two image capture stations include different station interfaces for retrieving said generated medical images therefrom, and said processing system includes a plurality of station interfaces to interface different ones of said remote image capture stations to retrieve said medical images;
  (b) storing said retrieved medical images from said image capture stations and associated information in a storage system of said processing system;
  (c) processing requests from at least one remote viewing station for said retrieved medical images and enabling transference of said requested medical images to said at least one remote viewing station, and generating a user interface for display and manipulation of said retrieved medical images; and
  (d) establishing communications over said network to enable said medical image retrieval and remote access to said retrieved medical images.

30. The method of claim 29, wherein said medical images include ophthalmic images.

31. The method of claim 29, wherein said storage system includes a database and a file system, and step (b) further includes:
  (b.1) generating a code for each medical image based on data within that image;
  (b.2) storing said code associated with each medical image within said database; and
  (b.3) storing said retrieved medical images within said file system.

32. The method of claim 31, wherein step (b) further includes:
  (b.4) detecting changes in medical images subsequent storage in said file system based on a change in said associated code.

33. The method of claim 31 further including:
  (e) generating a code for a retrieved medical image of said user interface and comparing said generated code to said code for that image stored in said database; and
  (f) displaying said user interface from said processing system including retrieved medical images at a viewing station in response to validation of said retrieved medical images.

34. The method of claim 33, wherein said network includes the Internet and each said viewing station includes a browser to display said user interface.

35. The method of claim 34, wherein said browser includes image manipulation controls, and step (f) further includes:
  (f.1) manipulating medical images displayed on a viewing station in accordance with actuation of said image manipulation controls by a user.

36. The method of claim 34, wherein said browser includes image measurement controls, and step (f) further includes:
  (f.1) measuring areas within said medical images displayed on a viewing station in accordance with actuation of said image measurement controls by a user.

37. The method of claim 36, wherein step (f.1) further includes:
  (f.1.1) selecting image resolution prior to performing measurement of said areas.

38. The method of claim 34, wherein step (f) further includes:
  (f.1) maintaining display settings during display of said medical images by said user on a viewing station.

39. The method of claim 31, wherein said file system stores said retrieved medical images and compressed versions of those medical images, and step (b) further includes:
  (b.4) selectively performing storage back-up operations for said information within said storage system, wherein said back-up operations include storing at least one of: said codes within said database; said codes and said compressed versions of said medical images; and said codes, said medical images and said compressed versions of said medical images.

40. The method of claim 29 further including:
  (e) transferring functions of said processing system to a redundant processing system in response to a failure of said processing system, wherein said redundant processing system stores information from said processing system and lags said processing system with respect to said stored information by a predetermined interval.

41. The method of claim 29 further including:
  (e) detecting various conditions of at least one of said processing system and said network and reporting said conditions to a remote system operations center without requiring a private network connection to said remote system operations center.

42. The method of claim 29, wherein step (c) further includes:
  (c.1) storing information pertaining to user sessions including at least one of users accessing said system, time of access and patients accessed by said user;
  (c.2) terminating a user session in response to predetermined conditions; and (c.3) controlling information accessed by said user, wherein said access is at least one of unlimited, limited to medical examination information associated with said user and limited to test case information.

43. The method of claim 29, wherein step (c) further includes:
(c.1) generating a user interface for displaying a plurality of medical images for comparison of those images by a user.

44. The method of claim 29, wherein step (c) further includes:
(c.1) enabling a user to verify a medical image retrieved from said image capture stations and indicating a verification status of said retrieved medical images.

45. The method of claim 44, wherein step (c.1) further includes:
(c.1.1) indicating a status of a medical image as unverified in response to modifications to that image.

46. The method of claim 29, wherein step (c) further includes:
(c.1) enabling a user in the form of a medical practitioner to review a medical image retrieved from said image capture stations and indicating a review status of said retrieved medical images.

47. The method of claim 46, wherein step (c.1) further includes:
(c.1.1) indicating a medical image lacks review in response to modifications to that image.

48. The method of claim 29, wherein step (b) further includes:
(b.1) transferring medical images from said storage system to locations local to said at least one viewing station prior to requests for those images from said at least one viewing station.

49. The method of claim 48, wherein a plurality of gateway units are each disposed at a different site remote from said processing system with each gateway unit coupled to said processing system and a corresponding image capture station, and step (b.1) further includes:
(b.1.1) receiving medical images from an image capture station at a corresponding gateway unit;
(b.1.2) generating compressed versions of said retrieved medical images at that gateway unit;
(b.1.3) storing said retrieved medical images and said compressed images in a cache memory of that gateway unit; and
(b.1.4) transferring said stored images from that gateway unit to said processing system.

50. The method of claim 49, wherein step (b.1.4) further includes:
(b.1.4.1) transferring said compressed images to said processing system prior to transference of said uncompressed medical images.

51. The method of claim 50, wherein step (b.1.4.1) further includes:
(b.1.4.1.1) transferring uncompressed medical images at times of low utilization of said network.

52. The method of claim 49, wherein at least one viewing station includes a cache memory, and step (b.1) further includes:
(b.1.5) transferring medical images from said storage system to at least one of said viewing station cache memory and said gateway unit cache memory.

53. The method of claim 52, wherein step (c) further includes:
(c.1) determining a location of a user accessing said processing system; and
(c.2) directing retrieval of a requested image from an image location in accordance with said user location and a storage location of said requested image, wherein said image location includes one of a cache memory of a viewing station of said user, a cache memory of a gateway unit local to said user and said storage system.

54. The method of claim 29, wherein a medical information system maintains information associated with patients and is coupled to said processing system via said network, said method further comprising:
(e) accessing said medical images from said medical information system.

55. The method of claim 54, wherein said network includes the Internet, and step (e) further includes:
(e.1) calling an Internet address of said processing system from said medical information system, wherein said call includes parameters to access desired information.

56. The method of claim 54, wherein step (e) further includes:
(e.1) accessing said processing system via networking protocols to transfer information between said medical information system and said processing system; and
(e.2) verifying patient information received from said medical information system with information associated with said medical images of said processing system and identifying medical images associated with information inconsistent with said information from said medical information system.

* * * * *

UNITED STATES PATENT AND TRADEMARK OFFICE
CERTIFICATE OF CORRECTION

| | | |
|---|---|---|
| PATENT NO. | : 7,818,041 B2 | |
| APPLICATION NO. | : 11/175410 | |
| DATED | : October 19, 2010 | |
| INVENTOR(S) | : Young Kim et al. | |

It is certified that error appears in the above-identified patent and that said Letters Patent is hereby corrected as shown below:

Column 8, line 44, replace "topology employing cashing" with -- topology employing caching --.

Signed and Sealed this
Twenty-third Day of August, 2011

David J. Kappos
*Director of the United States Patent and Trademark Office*